US008916137B2

(12) United States Patent
Hilderbrand et al.

(10) Patent No.: US 8,916,137 B2
(45) Date of Patent: Dec. 23, 2014

(54) MONOFUNCTIONAL CARBOCYANINE DYES FOR IN VIVO AND IN VITRO IMAGING

(75) Inventors: Scott A. Hilderbrand, Swampscott, MA (US); Ralph Weissleder, Charlestown, MA (US); Fangwei Shao, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 558 days.

(21) Appl. No.: 13/127,894

(22) PCT Filed: Nov. 9, 2009

(86) PCT No.: PCT/US2009/063750
§ 371 (c)(1),
(2), (4) Date: Aug. 15, 2011

(87) PCT Pub. No.: WO2010/054330
PCT Pub. Date: May 14, 2010

(65) Prior Publication Data
US 2011/0286933 A1    Nov. 24, 2011

Related U.S. Application Data

(60) Provisional application No. 61/112,535, filed on Nov. 7, 2008.

(51) Int. Cl.
| A61B 10/00 | (2006.01) |
| A61B 5/00 | (2006.01) |
| A61B 8/00 | (2006.01) |
| C07D 209/08 | (2006.01) |
| A61K 49/00 | (2006.01) |
| C07C 229/12 | (2006.01) |
| C07C 229/34 | (2006.01) |
| C07C 271/54 | (2006.01) |
| C09B 23/01 | (2006.01) |
| C09B 23/08 | (2006.01) |
| C09B 23/16 | (2006.01) |

(52) U.S. Cl.
CPC .......... *C07D 209/08* (2013.01); *A61K 49/0032* (2013.01); *C07C 229/12* (2013.01); *C07C 229/34* (2013.01); *C07C 271/54* (2013.01); *C09B 23/0008* (2013.01); *C09B 23/083* (2013.01); *C09B 23/086* (2013.01); *C09B 23/166* (2013.01)
USPC ............................. 424/9.6; 424/1.65; 424/9.1

(58) Field of Classification Search
CPC ........... A61K 49/0032; A61K 49/0056; A61K 49/0021; A61K 41/0057; A61K 41/0033; A61K 49/00; A61K 49/0004; A61K 49/001; A61K 49/0013; A61K 49/0017; A61K 49/0019; A61K 49/005; A61K 49/0052; A61K 49/0054; A61K 49/0058; C07D 207/30; C07D 207/00; C07D 295/00; C07D 209/04; C07D 209/08; C09B 23/00; C09B 23/0008; C09B 23/005; C09B 23/0066; C09B 23/0075; C09B 23/02; C09B 23/04; C09B 23/06; C09B 23/08; C09B 23/166; C09B 23/083; C09B 23/086; C07C 229/12; C07C 271/54; C07C 229/34
USPC .................. 424/1.11, 1.65, 9.6; 548/400, 560
See application file for complete search history.

(56) References Cited

U.S. PATENT DOCUMENTS

| 7,128,896 B2 * | 10/2006 | Achilefu et al. ............... 424/9.6 |
| 2005/0249668 A1 | 11/2005 | Weissleder et al. |
| 2007/0203343 A1 | 8/2007 | West et al. |

OTHER PUBLICATIONS

Lin Yuhui et al. Bioconjugate Chem. 2002, vol. 13, pp. 605-610.
Hilderbrand A. Scott et al. Chem. Commun. 2007, pp. 2747-2749.
International Search Report & Written Opinion, Patent Cooperation Treaty, PCT application No. PCT/US2009/063750; date of issuance May 10, 2011; 6 pages.
Abbs et al., "Sparing of first dose effect of monovalent anti-CD3 antibody used in allograft rejection is associated with diminished release of pro-inflammatory cytokines," *Ther. Immunol.*, 1994, 1(6):325-331.
Abe et al., "Correlation of In Vitro Autofluorescence Endoscopy Images With Histopathologic Findings in Stomach Cancer," *Endoscopy*, 2000, 32:281-286.
Alexander, "Lasers investigated as diagnostic tools for breast cancer," *J. Clin. Laser Med. Surg.*, 1991, 9:416-418.
Alfano et al., "Advances in Optical Imaging of Biomedical Media," *Ann. NY Acad. Sci.*, 1997, 820:248-270.
Ballou et al., "Fluorescence Imaging of Tumors In Vivo," *Curr. Med. Chem.*, 2005, 12;795-805.
Baskin et al., "Copper-free click chemistry for dynamic in vivo imaging," *Proc. Natl. Acad. Sci. USA*, 2007, 104:16793-16797.
Boas et al., "Scattering of diffuse photon density waves by spherical inhomogeneities within turbid media: analytic solution and applications," *Proc. Natl. Acad. Sci. USA*, 1994, 91:4887-4891.
Boppart et al., "Noninvasive assessment of the developing *Xenopus* cardiovascular system using optical coherence tomography," *Proc. Natl. Acad. Sci. USA*, 1997, 94:4256-4261.
Chance, "Near-Infrared Images Using Continuous, Phase-Modulated, and Pulsed Light With Quantitation of Blood and Blood Oxygenation," *Ann. NY Acad. Sci.*, 1998, 838:29-45.
Cheng and Boas, "Diffuse optical reflection tomography using continuous wave illumination," *Optics Express*, 1998, 3(3):118-123.
Claus, "Schreiber onzonolysis was decidedly superior to a more classical route proceeding through Michael addition of malonic ester to acrolein cf," *Org. Synth. Coll.*, 1990, 7:168-171.
Colcher et al., "Single-Chain Antibodies in Pancreatic Cancer,"*Ann. N.Y. Acad. Sci.*, 1999, 880:263-280.
Cortez-Retamozo et al., "Real-time assessment of inflammation and treatment response in a mouse model of allergic airway inflammation," *J. Clin. Invest.*, 2008, 118:4058-4066.

(Continued)

*Primary Examiner* — D L Jones
(74) *Attorney, Agent, or Firm* — Fish & Richardson P.C.

(57) ABSTRACT

The present invention provides symmetric carbocyanine dyes and dye precursors useful for fluorescence microscopy, and methods of making and using same.

6 Claims, 11 Drawing Sheets

(56) References Cited

OTHER PUBLICATIONS

Dellian et al., "Vascular permeability in a human tumour xenograft: molecular charge dependence," *Br. J. Cancer*, 2000, 82:1513-1518.
Fukumura et al., "Tumor induction of VEGF promoter activity in stromal cells," *Cell*, 1998, 94:715-725.
Gahlen et al., "Spectrometry Supports Fluorescence Staging Laparoscopy After Intraperitoneal Aminolaevulinic Acid Lavage for Gastrointestinal Tumours," *J. Photochem. Photobiol. B Biol.*, 1999, 52:131-135.
Goding, "Purification, Fragmentation and Isotopic Labelling of Monoclonal Antibodies," *Monoclonal Antibodies: Principles and Practice*, NY Academic Press, 1983, 98-118.
Goncalves, "Fluorescent Labeling of Biomolecules With Organic Probes," *Chem. Rev.*, 2009, 109:190-212.
Gonzalez et al., "Characterization of psoriasis in vivo by reflectance confocal microscopy," *J. Med.*, 1999, 30:337-356.
Hilderbrand et al., "Monofunctional Near-Infrared Fluorochromes for Imaging Applications," *Bioconjug. Chem.*, 2005, 16:1275-1281.
Hsu et al., "Alkynyl sugar analogs for the labeling and visualization of glycoconjugates in cells," *Proc. Natl. Acad. USA*, 2007, 104:2614-2619.
International Preliminary Report on Patentability in International Application No. PCT/US2009/063750, dated May 10, 2011, 7 pages.
International Search Report & Written Opinion in International Application No. PCT/US2009/063750, dated Jul. 1, 2010, 11 pages.
Izuishi et al., "Detection of bile duct cancer by autofluorescence cholangioscopy: a pilot study," *Hepatogastroenterology*, 1999, 46:804-807.
Berge, "Pharmaceutical Salts," *Journal of Pharmaceutical Science*, Jan. 1977, 66:2-19.
Korlach et al., "Characterization of lipid bilayer phases by confocal microscopy and fluorescence correlation spectroscopy," *Proc. Natl. Acad. Sci. USA*, 1999, 96:8461-8466.
Kriegmair et al., "5-Aminolevulinic Acid-Induced Fluorescence Endoscopy for the Detection of Lower Urinary Tract Tumors,"*Urol. Int.*, 1999, 63:27-31.
Leimgruber et al., "Behavior of endogenous tumor-associated macrophages assessed in vivo using a functionalized nanoparticle," *Neoplasia*, 2009, 11(5):459-468.
Lin et al., "Novel Near-Infrared Cyanine Fluorochromes: Synthesis, Properties, and Bioconjugation," *Bioconjug. Chem.*, 2002, 13:605-610.
Major et al., "In Vivo Fluorescence Detection of Ovarian Cancer in the Nutu-19 Epithelial Ovarian Cancer Animal Model Using 5-Aminolevulinic Acid (ALA)," *Gynecol. Oncol.*, 1997, 66:122-132.
McCarthy et al., "Targeted delivery of multifunctional magnetic nanoparticles," *Nanomed.*, 2007, 2(2):153-167.
Monsky et al., "Augmentation of transvascular transport of macromolecules and nanoparticles in tumors using vascular endothelial growth factor," *Cancer Res.*, 1999, 59:4129-4135.

Mujumdar et al., "Cyanine Dye Labeling Reagents: Sulfoindocyanine Succinimidyl Esters," *Bioconjug. Chem.*, Mar./Apr. 1993, 4(2):105-111.
Mujumdar et al., "Cyanine-Labeling Reagents: Sulfobenzindocyanine Succinimidyl Esters," *Bioconjug. Chem.*, 1996, 7:356-362.
Mycek et al., "Colonic Polyp Differentiation Using Time-Resolved Autofluorescence Spectroscopy," *Am. Soc. Gastrointest. Endosc.*, 1998, 48:390-394.
Narayana and Patonay, "A New Method for the Synthesis of Heptamethine Cyanine Dyes: Synthesis of New Near-Infrared Fluorescent Labels," *J. Org. Chem.*, 1995, 60:2391-2395.
Ntziachristos et al., "Concurrent MRI and diffuse optical tomography of breast after indocyanine green enhancement," *Natl. Acad. Sci. USA*, 2000, 97:2767-2772.
Pham et al., "Synthesis and Application of a Water-Soluble Near-Infrared Dye for Cancer Detection Using Optical Imaging," *Bioconjug. Chem.*, 2005, 16:735-740.
Reiter, "Antibody engineering of recombinant Fv immunotoxins for improved targeting of cancer: disulfide-stabalized Fv immunotoxins," *Clinical Cancer Res.*, 1996, 2:245-252.
Riedl et al., "Fluorescence detection of bladder tumors with 5-aminolevulinic acid," *J. Endourol.*, 1999, 13:755-759.
Rajadhyaksha et al., "In Vivo Confocal Scanning Laser Microscopy of Human Skin: Melanin Provides Strong Contrast," *J. Invest. Dermatol.*, 1995, 104(6):946-952.
Ross et al., "Anticancer Antibodies," *Am. J Clin. Pathol.*, 2003, 119(4): 472-485.
Sawa et al., "Glycoproteomic probes for fluorescent imaging of fucosylated glycans in vivo," *Proc. Natl. Acad. Sci. USA*, 2006, 103:12371-12376.
Shao et al., "Monofunctional carbocyanine dyes for bio- and bioorthogonal conjugation," *Bioconjug. Chem.*, 2008, 19:2487.
Siegel et al., "Design and evaluation of a continuous-wave diffuse optical tomography system," *Optics Express*, 1999, 4:287-298.
Sosnovik et al., "Targeted imaging of myocardial damage," *Nat. Clin. Pract. Card.*, 2008, 5:S63.
Stepp et al., "Fluorescence endoscopy of gastrointestinal diseases: basic principles, techniques, and clinical experience," *Endoscopy*, 1998, 30:379-386.
Tearney et al., "In Vivo Endoscopic Optical Biopsy With Optical Coherence Tomography," *Science*, Jun. 27, 1997, 276:2037-2039.
Ward, "New Laser Techniques for Diagnosis and Treatment of Deep-Seated Brain Lesions," *J. Laser Appl.*, 1998, 10:224-228.
Weissleder and Ntziachristos, "Shedding Light Onto Live Molecular Targets," *Nat. Med.*, 2003, 9(1):123-128.
Weissleder et al., "In Vivo Imaging of Tumors With Protease-Activated Near-Infrared Fluorescent Probes," *Nat. Biotechnol.*, Apr. 1999, 17:375-378.
Weissleder, "A Clearer Vision for in Vivo Imaging," *Nat. Biotechnol.*, Apr. 2001, 19:316-317.

* cited by examiner

Table 1. Optical properties of pentamethine carbocyanine dyes.

| | $\lambda_{abs}$ (nm)[a] | $\lambda_{em}$ (nm) | $\varepsilon$ (M$^{-1}$cm$^{-1}$)[b] | $\Phi$[c] |
|---|---|---|---|---|
| CyAM-5 acid | 642 | 656 | 215000 | 0.17 |
| CyAM-5 azide | 641 | 658 | 222000 | 0.20 |
| CyAM-5 alkyne | 641 | 657 | 240000 | 0.20 |

|  | $\lambda_{max,abs}(nm)^a$ | $\lambda_{max,em}(nm)$ | $\varepsilon$ $(M^{-1}cm^{-1})^b$ | $\Phi^c$ |
|---|---|---|---|---|
| CyAL-5 | 641 | 658 | 233,000 | 0.13 |
| CyAL-5.5 | 674 | 691 | 157,000 | 0.12 |

FIG. 9

MONOFUNCTIONAL CARBOCYANINE DYES FOR IN VIVO AND IN VITRO IMAGING

STATEMENT REGARDING FEDERALLY SPONSORED RESEARCH OR DEVELOPMENT

The present invention was made with government support Under Grant No. 1-01-HL080731 awarded by the National Institutes of Health. The United States Government has certain rights in the invention.

CLAIM OF PRIORITY

This application is the national stage of International Application Number PCT/US2009/063750, filed on Nov. 9, 2009, which is based on and claims the benefit of U.S. Provisional Patent Application Ser. No. 61/112,535, filed on Nov. 7, 2008, the entire contents of which are hereby incorporated by reference all of which as filed are incorporated herein by reference in their entireties.

FIELD OF THE INVENTION

The present invention provides symmetric carbocyanine dyes with far-red/near infrared (NIR) emission useful for biochemical and in vivo imaging applications.

BACKGROUND OF THE INVENTION

Fluorescent chromophores play an essential role in molecular imaging both in vitro and in vivo (Goncalves, M. S. *Chem. Rev.* 2009, 109, 190). Of these fluorescent reporters, far-red and near infrared (NIR) dyes have ideal absorption/emission wavelengths between 600 and 1000 nm, which minimize autofluorescence interference from tissue and have minimal overlap with biological chromophores such as haemoglobin (Weissleder, R.; Ntziachristos, V. *Nat. Med.* 2003, 9, 123). NIR fluorophores have become the best candidates for use in fluorescent tags and fluorogenic probes for in vivo imaging (Ballou, B.; Ernst, L. A.; Waggoner, A. S. *Curr. Med. Chem.* 2005, 12, 795; Weissleder, R.; Tung, C. H.; Mahmood, U.; Bogdanov, A., Jr. *Nat. Biotechnol.* 1999, 17, 375). For example, NIR dyes conjugated to peptides or nanoparticles have successfully been applied to in vivo imaging of tumors, (Ballou, B.; Ernst, L. A.; Waggoner, A. S. *Curr. Med. Chem.* 2005, 12, 795; Weissleder, R.; Tung, C. H.; Mahmood, U.; Bogdanov, A., Jr. *Nat. Biotechnol.* 1999, 17, 375; Weissleder. *Nat. Biotechnol.* 2001, 10, 316; Leimgruber, A. B. C.; Cortez-Retamozo, V.; Etzrodt, M.; Newton, A. P.; Waterman P.; Figueiredo, J. L.; Kohler, R. H.; Elpek, N.; Mempel, T. R.; Swirski, F. K.; Nahrendorf, M.; Weissleder, R.; Pittet, M. J. *Neoplasia* 2009, 11) myocardial infraction (Sosnovik, D.; Nahrendorf, M.; Weissleder, R. *Nat. Clin. Pract. Card.* 2008, 5, S63) and inflammation (Cortez-Retamozo, V.; Swirski, F. K.; Waterman, P.; Yuan, H.; Figueiredo, J. L.; Newton, A. P.; Upadhyay, R.; Vinegoni, C.; Kohler, R.; Blois, J.; Smith, A.; Nahredorf, M.; Josephson, L.; Weissleder, R.; Pittet, M. *J. Clin. Invest.* 2008, 118, 4058).

Carbocyanine fluorophores are one of the canonical NIR dye families with excellent optical properties, including tunable NIR emission, high extinction coefficients, and good fluorescence quantum yields (Hilderbrand, S. A.; Kelly, K. A.; Weissleder, R.; Tung, C. H. *Bioconjug. Chem.* 2005, 16, 1275). Since the 1980s, a variety of carboxylic acid derivatized carbocyanines have been prepared to meet the increasing demand for their use in bioconjugation and imaging applications (Mujumdar, S. R.; Mujumdar, R. B.; Grant, C. M.; Waggoner, A. S. *Bioconjug. Chem.* 1996, 7, 356; Mujumdar, R. B.; Ernst, L. A.; Mujumdar, S. R.; Lewis, C. J.; Waggoner, A. S. *Bioconjug. Chem.* 1993, 4, 105). However, their widespread use is hindered by the high cost and limited availability of large quantities for many of these fluorescent labels. Most monofunctional carbocyanine dyes are asymmetric with the conjugation handle attached to one of the quaternary nitrogens of the indolium or benzo[e]indolium moieties. During the synthesis of these asymmetric dyes, undesired symmetric dyes are also formed (FIG. 1). These symmetric dye byproducts are often difficult to separate from the desired monofunctional dyes and contribute to decreased synthetic yields, often lower than 10% (Lin, Y.; Weissleder, R.; Tung, C. H. *Bioconjug. Chem.* 2002, 13, 605).

SUMMARY OF THE INVENTION

Provided herein are simple, high-yielding synthetic routes to monofunctional carbocyanine labels that are useful in a variety of biochemical and in vivo imaging settings.

Accordingly, in a first aspect the present invention provides, inter alia, a carbocyanine dye of Formula I:

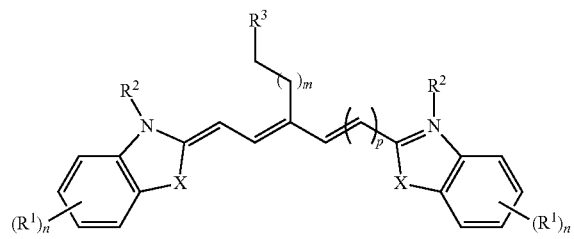

or a pharmaceutically acceptable salt thereof, wherein:

X is selected from O, NH, N(CH$_3$), S, Se, Te, C(CH$_3$)$_2$;

R$^1$ is selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, S(O)$_2$NR$^C$R$^D$, and P(OR$^B$)$_2$, wherein said C$_{1-6}$ alkyl is optionally substituted by S(O)$_2$R$^B$, NR$^C$R$^D$, or C(O)OR$^A$;

or 2 R$^1$ adjacent to each other and together with the C atoms to which they are attached form an aryl ring, optionally substituted by 1, 2, 3, or 4 substituents independently selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, and S(O)$_2$NR$^C$R$^D$, P(OR$^B$)$_2$, wherein said C$_{1-6}$ alkyl is optionally substituted by S(O)$_2$R$^B$, NR$^C$R$^D$, or C(O)OR$^A$;

R$^2$ is C$_{1-6}$ alkyl, C$_{1-6}$ haloalkyl, C$_{2-6}$ alkenyl, C$_{2-6}$ alkynyl, wherein said C$_{1-6}$ alkyl, is optionally substituted by S(O)$_2$R$^B$, NR$^C$R$^D$, or C(O)OR$^A$;

R$^3$ is selected from C(O)OR$^A$ and C(O)NR$^B$R$^C$;

R$^A$, R$^B$, R$^C$ and R$^D$ are independently selected from H, C$_{1-6}$ alkyl, aryl or succinimidyl, wherein said C$_{1-6}$ alkyl and aryl is optionally substituted with 1, 2, 3, or 4 substituents selected from C(O)OR$^{a1}$, C$_{2-6}$ alkenyl, C$_{2-6}$ alkynyl, N$_3$, C(O)R$^{b1}$, OR$^{a1}$, SR$^{a1}$, NR$^{c1}$R$^{d1}$, —S(O)$_2$Cl hydrazide, hydrazine, or maleimide;

R$^{a1}$, R$^{b1}$, R$^{c1}$ and R$^{d1}$ are independently selected from H and C$_{1-6}$ alkyl;

m is 0, 1, 2, 3, 4, 5, 6, 7, 8, 9, or 10;

n is 1, 2, 3, or 4; and p is 1 or 2.

In one embodiment, the invention provides a carbocyanine dye, or a pharmaceutically acceptable salt thereof, selected from:
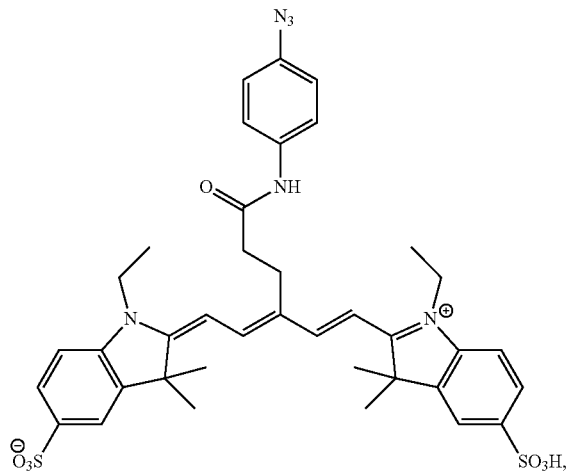
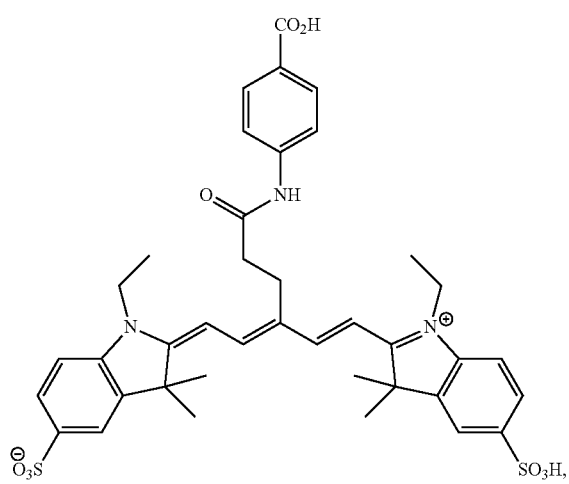
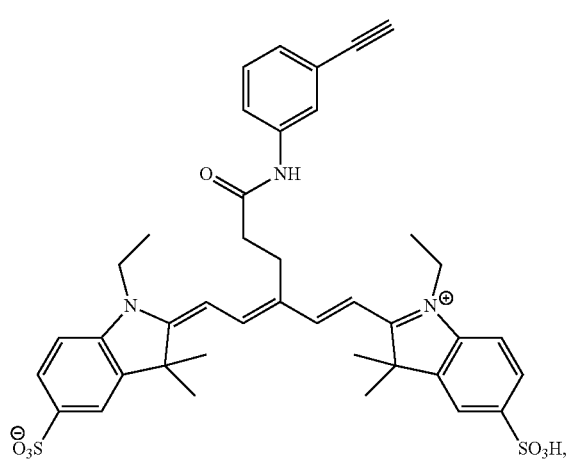
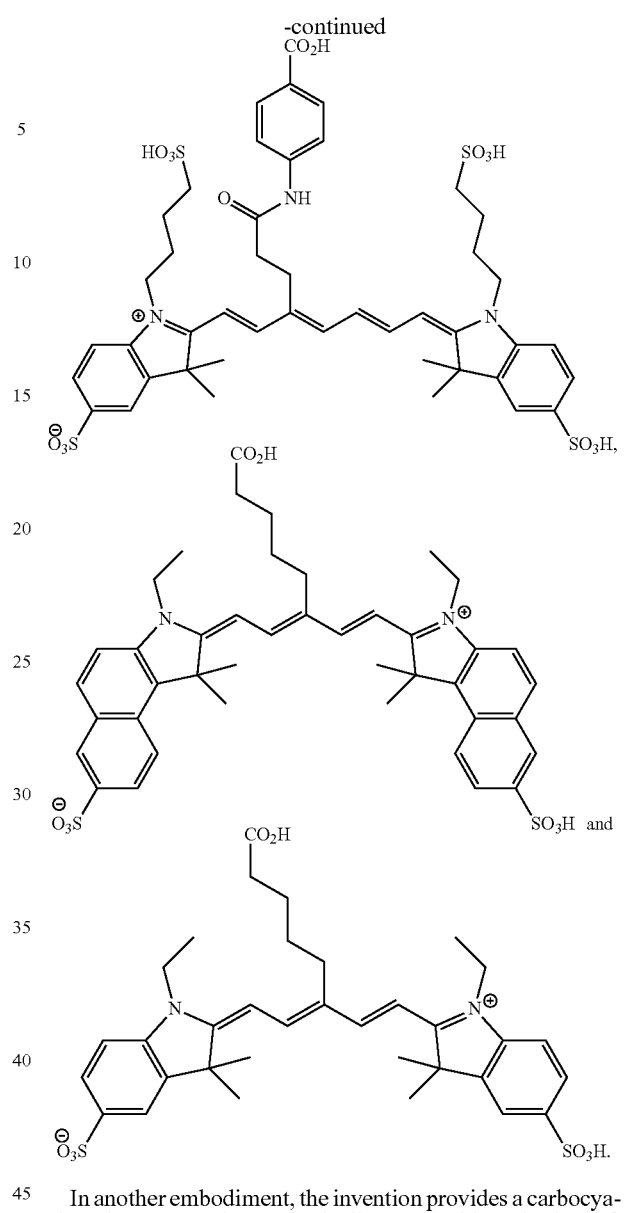
In another embodiment, the invention provides a carbocyanine dye, or a pharmaceutically acceptable salt thereof, selected from:
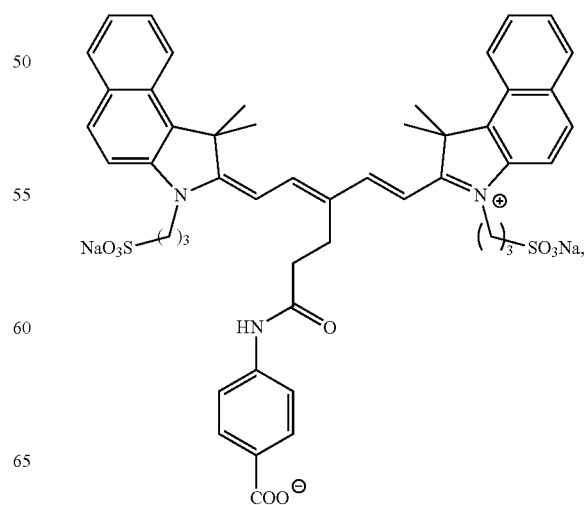

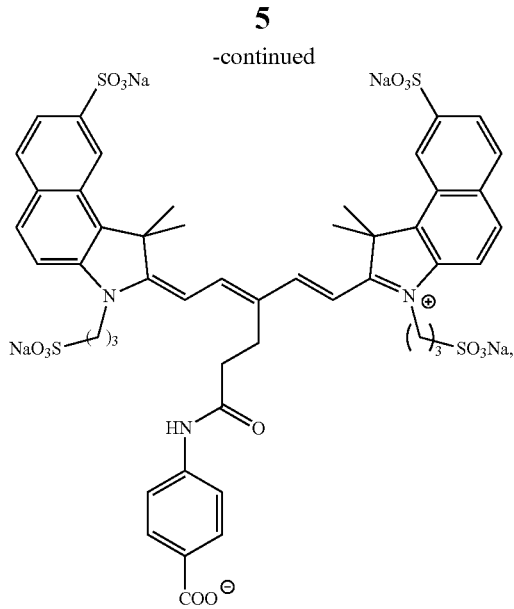

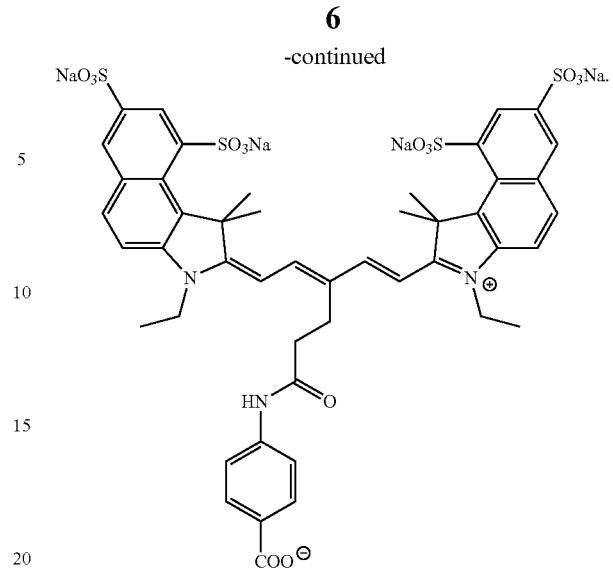

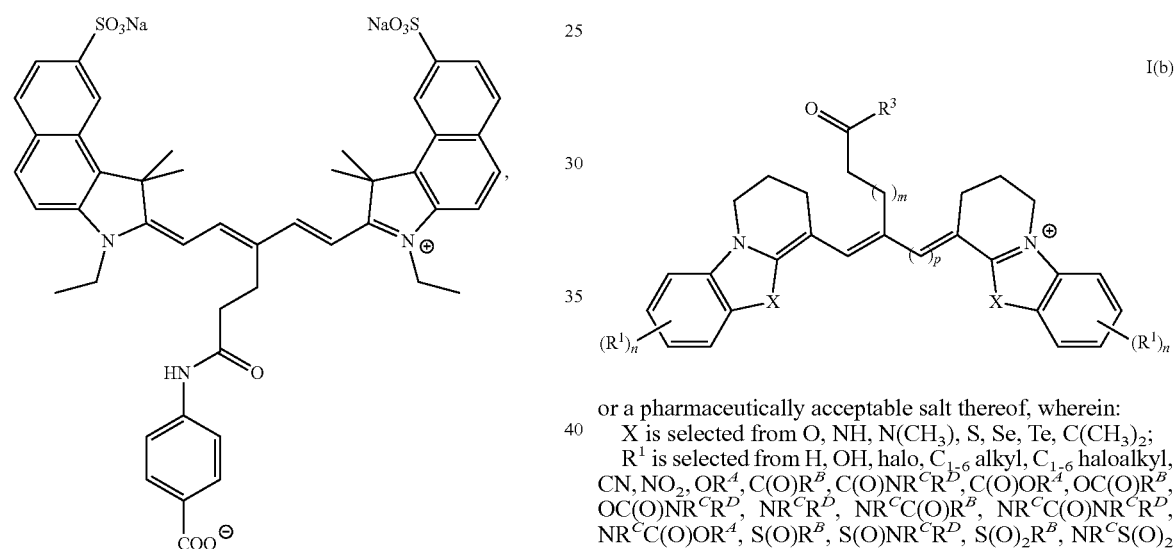

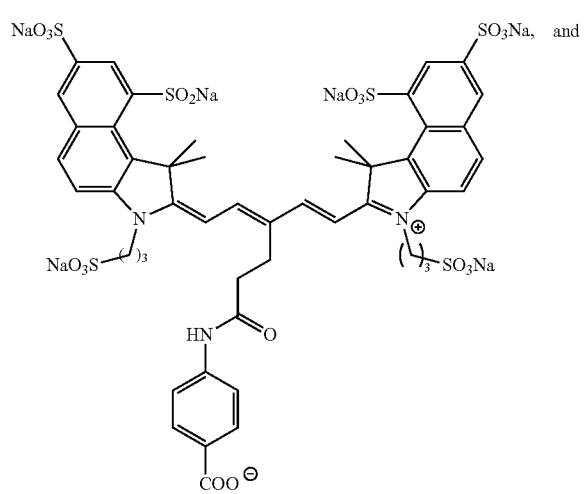

In one aspect, the invention provides a carbocyanine dye of Formula I(b):

I(b)

or a pharmaceutically acceptable salt thereof, wherein:

X is selected from O, NH, N(CH$_3$), S, Se, Te, C(CH$_3$)$_2$;

R$^1$ is selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, S(O)$_2$NR$^C$R$^D$, and P(OR$^B$)$_2$, wherein said C$_{1-6}$ alkyl is optionally substituted by S(O)$_2$R$^B$, NR$^C$R$^D$, or C(O)OR$^A$;

or 2 R$^1$ adjacent to each other and together with the C atoms to which they are attached form an aryl group, optionally substituted by 1, 2, 3, or 4 substituents independently selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, and S(O)$_2$NR$^C$R$^D$, P(OR$^B$)$_2$, wherein said C$_{1-6}$ alkyl is optionally substituted by S(O)$_2$R$^B$, NR$^C$R$^D$, or C(O)OR$^A$;

R$^2$ is C$_{1-6}$ alkyl, C$_{1-6}$ haloalkyl, C$_{2-6}$ alkenyl, C$_{2-6}$ alkynyl, wherein said C$_{1-6}$ alkyl, is optionally substituted by S(O)$_2$R$^B$, NR$^C$R$^D$, or C(O)OR$^A$;

R$^3$ is selected from C(O)OR$^A$ and C(O)NR$^B$R$^C$;

R$^A$, R$^B$, R$^C$ and R$^D$ are independently selected from H, C$_{1-6}$ alkyl, aryl or succinimidyl, wherein said C$_{1-6}$ alkyl and aryl is optionally substituted with 1, 2, 3, or 4 substituents selected from C(O)OR$^{a1}$, C$_{2-6}$ alkenyl, C$_{2-6}$ alkynyl, N$_3$, C(O)R$^{b1}$, OR$^{a1}$, SR$^{a1}$, NR$^{c1}$R$^{d1}$, —S(O)$_2$Cl hydrazide, hydrazine, or maleimide;

R$^{a1}$, R$^{b1}$, R$^{c1}$ and R$^{d1}$ are independently selected from H and C$_{1-6}$ alkyl;

m is 0, 1, 2, 3, 4, 5, 6, 7, 8, 9, or 10;
n is 1, 2, 3, or 4; and
p is 1 or 2.

In one embodiment, the invention provides a carbocyanine dye of claim 4, or a pharmaceutically acceptable salt thereof, having the structure:

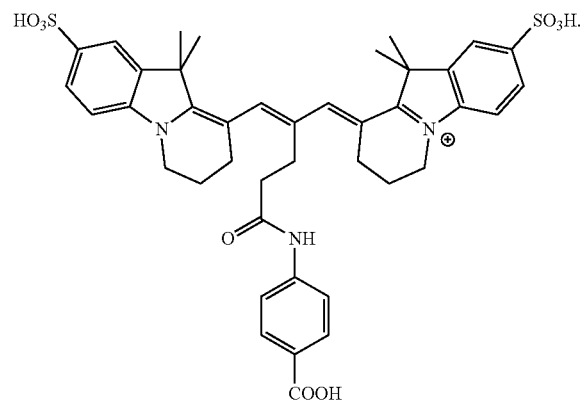 [SMILES: CC1(C)C2=C(/C=C(/C=C3\CCC[N+]4=C3C(C)(C)c3cc(S(=O)(=O)O)ccc34)CCC(=O)Nc3ccc(C(=O)O)cc3)CCCN2c2ccc(S(=O)(=O)O)cc21]

In one aspect, the invention provides a process for preparing a carbocyanine dye of Formula I:

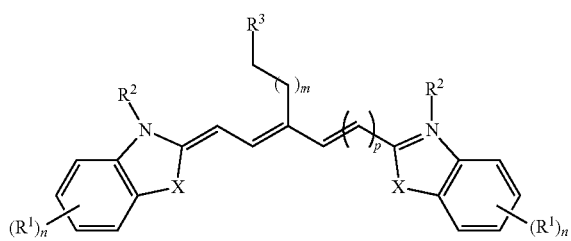

or a pharmaceutically acceptable salt thereof, wherein:
X is selected from O, NH, N(CH$_3$), S, Se, Te, C(CH$_3$)$_2$;
R$^1$ is selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, S(O)$_2$NR$^C$R$^D$, and P(OR$^B$)$_2$, wherein said C$_{1-6}$ alkyl is optionally substituted by S(O)$_2$R$^B$, NR$^C$R$^D$, or C(O)OR$^A$;

or 2 R$^1$ adjacent to each other and together with the C atoms to which they are attached form an aryl ring, optionally substituted by 1, 2, 3, or 4 substituents independently selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, and S(O)$_2$NR$^C$R$^D$, P(OR$^B$)$_2$, wherein said C$_{1-6}$ alkyl is optionally substituted by S(O)$_2$R$^B$, NR$^C$R$^D$, or C(O)OR$^A$;

R$^2$ is C$_{1-6}$ alkyl, C$_{1-6}$ haloalkyl, C$_{2-6}$ alkenyl, C$_{2-6}$ alkynyl, wherein said C$_{1-6}$ alkyl, is optionally substituted by S(O)$_2$R$^B$, NR$^C$R$^D$, or C(O)OR$^A$;

R$^3$ is selected from C(O)OR$^A$ and C(O)NR$^B$R$^C$;

R$^A$, R$^B$, R$^C$ and R$^D$ are independently selected from H, C$_{1-6}$ alkyl, aryl or succinimidyl, wherein said C$_{1-6}$ alkyl and aryl is optionally substituted with 1, 2, 3, or 4 substituents selected from C(O)OR$^{a1}$, C$_{2-6}$ alkenyl, C$_{2-6}$ alkynyl, N$_3$, C(O)R$^{b1}$, OR$^{a1}$, SR$^{a1}$, NR$^{c1}$R$^{d1}$, —S(O)$_2$Cl hydrazide, hydrazine, or maleimide;

R$^{a1}$, R$^{b1}$, R$^{c1}$ and R$^{d1}$ are independently selected from H and C$_{1-6}$ alkyl;
m is 0, 1, 2, 3, 4, 5, 6, 7, 8, 9, or 10;
n is 1, 2, 3, or 4; and
p is 1 or 2;
comprising:
reacting a malonaldeyhyde dianil of Formula I-(1):

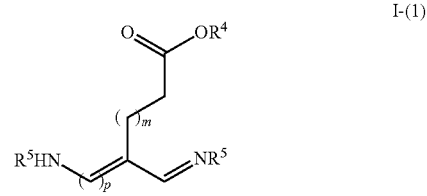

or a pharmaceutically acceptable salt thereof, wherein:
R$^4$ is selected from H and C$_{1-6}$ alkyl;
R$^5$ is selected from C$_{1-6}$ alkyl and aryl, wherein said C$_{1-6}$ alkyl and aryl is optionally substituted with a substituent selected from C(O)OR$^A$, C$_{2-6}$ alkenyl, C$_{2-6}$ alkynyl, N$_3$, C(O)R$^B$, OR$^A$, SR$^A$, NR$^C$R$^D$, —S(O)$_2$Cl, hydrazide, hydrazine, or maleimide;

R$^A$, R$^B$, R$^C$ and R$^D$ are independently selected from H, C$_{1-4}$ alkyl, aryl or succinimidyl, wherein said C$_{1-6}$ alkyl and aryl is optionally substituted with 1, 2, 3, or 4 substituents selected from C(O)OR$^{a1}$, C$_{2-6}$ alkenyl, C$_{2-6}$ alkynyl, N$_3$, C(O)R$^{b1}$, OR$^{a1}$, SR$^{a1}$, NR$^{c1}$R$^{d1}$, —S(O)$_2$Cl, hydrazide, hydrazine, or maleimide;

R$^{a1}$, R$^{b1}$, R$^{c1}$ and R$^{d1}$ are independently selected from H and C$_{1-6}$ alkyl;
m is 0, 1, 2, 3, 4, 5, 6, 7, 8, 9, or 10; and
p is 1 or 2;
with an indoleninium compound of Formula I-(2):

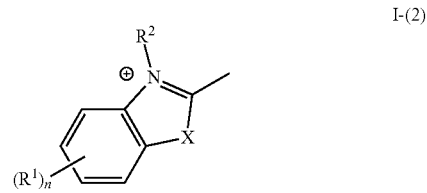

or a pharmaceutically acceptable salt thereof, wherein:
X is selected from O, NH, N(CH$_3$), S, Se, Te, C(CH$_3$)$_2$;
R$^1$ is selected from H, OH, halo, C$_{1-6}$ alkyl, C$_{1-6}$ haloalkyl, C$_{2-6}$ alkenyl, C$_{2-6}$ alkynyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, and S(O)$_2$NR$^C$R$^D$, P(OR$^B$)$_2$, wherein said C$_{1-6}$ alkyl is optionally substituted by S(O)$_2$R$^B$, NR$^C$R$^D$, or C(O)OR$^A$;

or 2 R$^1$ adjacent to each other and together with the C atoms to which they are attached form an aryl ring, optionally substituted by 1, 2, 3, or 4 substituents independently selected from H, OH, halo, C$_{1-6}$ alkyl, C$_{1-6}$ haloalkyl, CN, NO$_2$, OR$^A$, C(O)R$^B$, C(O)NR$^C$R$^D$, C(O)OR$^A$, OC(O)R$^B$, OC(O)NR$^C$R$^D$, NR$^C$R$^D$, NR$^C$C(O)R$^B$, NR$^C$C(O)NR$^C$R$^D$, NR$^C$C(O)OR$^A$, S(O)R$^B$, S(O)NR$^C$R$^D$, S(O)$_2$R$^B$, NR$^C$S(O)$_2$R$^B$, and S(O)$_2$NR$^C$R$^D$, P(OR$^B$)$_2$, wherein said C$_{1-6}$ alkyl is optionally substituted by S(O)$_2$R$^B$, NR$^C$R$^D$, or C(O)OR$^A$;

R$^2$ is C$_{1-6}$ alkyl, C$_{1-6}$ haloalkyl, C$_{2-6}$ alkenyl, C$_{2-6}$ alkynyl, wherein said C$_{1-6}$ alkyl, is optionally substituted by S(O)$_2$R$^B$, NR$^C$R$^D$, or C(O)OR$^A$;

$R^A$, $R^B$, $R^C$ and $R^D$ are independently selected from H, $C_{1-4}$ alkyl, aryl or succinimidyl, wherein said $C_{1-6}$ alkyl and aryl is optionally substituted with 1, 2, 3, or 4 substituents selected from $C(O)OR^{a1}$, $C_{2-6}$ alkenyl, $C_{2-6}$ alkynyl, $N_3$, $C(O)R^{b1}$, $OR^{a1}$, $SR^{a1}$, $NR^{c1}R^{d1}$, —$S(O)_2Cl$, hydrazide, hydrazine, or maleimide;

$R^{a1}$, $R^{b1}$, $R^{c1}$ and $R^{d1}$ are independently selected from H and $C_{1-6}$ alkyl; and n is 1, 2, 3, or 4;

via a condensation reaction to provide the carbocyanine dye of Formula I.

In one embodiment, the invention provides a method of imaging a biological target, the method comprising: contacting a targeting agent that binds specifically to the biological target with a carbocyanine dye, or its activated succinimidyl ester, for a time sufficient for the targeting agent and the carbocyanine dye to react and form a chemical bond, thereby labeling the targeting agent with the carbocyanine dye to provide a labeled targeting agent; contacting the biological target with the labeled targeting agent and providing a fluorescence image of the biological target labeled with the labeled targeting agent, thereby imaging the biological target.

In some embodiments, the targeting agent is an antibody. In another embodiment, the targeting agent is a protein. In another embodiment, the targeting agent is a peptide. In yet another embodiment, the targeting agent is a small molecule. In another embodiment, the targeting agent is a nucleic acid. In yet a further embodiment, the targeting agent is an aptamer. In yet another embodiment, the targeting agent is a surface-modified nanoparticles.

In some embodiments, the fluorescence image is provided by fluorescence microscopy.

In some embodiments, the method is carried out in vivo in a living cell.

In some embodiments, the biological target and the carbocyanine dye react via a bio-orthogonal conjugation reaction.

In some embodiments, the bio-orthogonal conjugation reaction is a 1,3-dipolar cycloaddition reaction.

In another aspect, the invention provides a carbocyanine dye precursor of Formula I-(2):

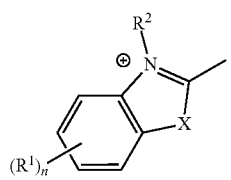

I-(2)

or a pharmaceutically acceptable salt thereof, wherein:
X is selected from O, NH, $N(CH_3)$, S, Se, Te, $C(CH_3)_2$;
$R^1$ is selected from H, OH, halo, $C_{1-6}$ alkyl, $C_{1-6}$ haloalkyl, $C_{2-6}$ alkenyl, $C_{2-6}$ alkynyl, CN, $NO_2$, $OR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, and $S(O)_2NR^CR^D$, $P(OR^B)_2$, wherein said $C_{1-6}$ alkyl is optionally substituted by $S(O)_2R^B$, $NR^CR^D$, or $C(O)OR^A$;

or 2 $R^1$ adjacent to each other and together with the C atoms to which they are attached form an aryl ring, optionally substituted by 1, 2, 3, or 4 substituents independently selected from H, OH, halo, $C_{1-6}$ alkyl, $C_{1-6}$ haloalkyl, CN, $NO_2$, $OR^A$, $C(O)R^B$, $C(O)NR^CR^D$, $C(O)OR^A$, $OC(O)R^B$, $OC(O)NR^CR^D$, $NR^CR^D$, $NR^CC(O)R^B$, $NR^CC(O)NR^CR^D$, $NR^CC(O)OR^A$, $S(O)R^B$, $S(O)NR^CR^D$, $S(O)_2R^B$, $NR^CS(O)_2R^B$, and $S(O)_2NR^CR^D$, $P(OR^B)_2$, wherein said $C_{1-6}$ alkyl is optionally substituted by $S(O)_2R^B$, $NR^CR^D$, or $C(O)OR^A$;

$R^2$ is $C_{1-6}$ alkyl, $C_{1-6}$ haloalkyl, $C_{2-6}$ alkenyl, $C_{2-6}$ alkynyl, wherein said $C_{1-6}$ alkyl, is optionally substituted by $S(O)_2R^B$, $NR^CR^D$, or $C(O)OR^A$;

$R^A$, $R^B$, $R^C$ and $R^D$ are independently selected from H, $C_{1-4}$ alkyl, aryl or succinimidyl, wherein said $C_{1-6}$ alkyl and aryl is optionally substituted with 1, 2, 3, or 4 substituents selected from $C(O)OR^{a1}$, $C_{2-6}$ alkenyl, $C_{2-6}$ alkynyl, $N_3$, $C(O)R^{b1}$, $OR^{a1}$, $SR^{a1}$, $NR^{c1}R^{d1}$, —$S(O)_2Cl$, hydrazide, hydrazine, or maleimide;

$R^{a1}$, $R^{b1}$, $R^{c1}$ and $R^{d1}$ are independently selected from H and $C_{1-6}$ alkyl; and n is 1, 2, 3, or 4.

In another aspect, the invention provides a malonaldeyhyde dianil of Formula I-(1):

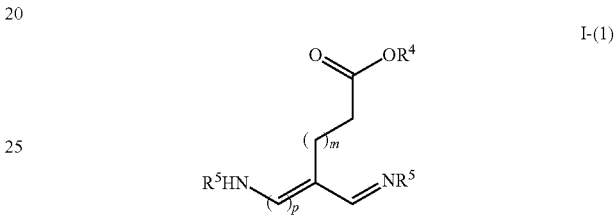

I-(1)

or a pharmaceutically acceptable salt thereof, wherein:
$R^4$ is selected from H and $C_{1-6}$ alkyl;
$R^5$ is selected from $C_{1-6}$ alkyl and aryl, wherein said $C_{1-6}$ alkyl and aryl is optionally substituted with a substituent selected from $C(O)OR^A$, $C_{2-6}$ alkenyl, $C_{2-6}$ alkynyl, $N_3$, $C(O)R^B$, $OR^A$, $SR^A$, $NR^CR^D$, —$S(O)_2Cl$, hydrazide, hydrazine, or maleimide;

$R^A$, $R^B$, $R^C$ and $R^D$ are independently selected from H, $C_{1-6}$ alkyl, aryl or succinimidyl, wherein said $C_{1-6}$ alkyl and aryl is optionally substituted with 1, 2, 3, or 4 substituents selected from $C(O)OR^{a1}$, $C_{2-6}$ alkenyl, $C_{2-6}$ alkynyl, $N_3$, $C(O)R^{b1}$, $OR^{a1}$, $SR^{a1}$, $NR^{c1}R^{d1}$, —$S(O)_2Cl$, hydrazide, hydrazine, or maleimide;

$R^{a1}$, $R^{b1}$, $R^{c1}$ and $R^{d1}$ are independently selected from H and $C_{1-6}$ alkyl;

m is 0, 1, 2, 3, 4, 5, 6, 7, 8, 9, or 10; and
p is 1 or 2.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 9 summarizes the optical properties of pentamethine carbocyanine dyes, CyAl-5 and CyAl-5.5.

DETAILED DESCRIPTION OF THE INVENTION

Figure 1:
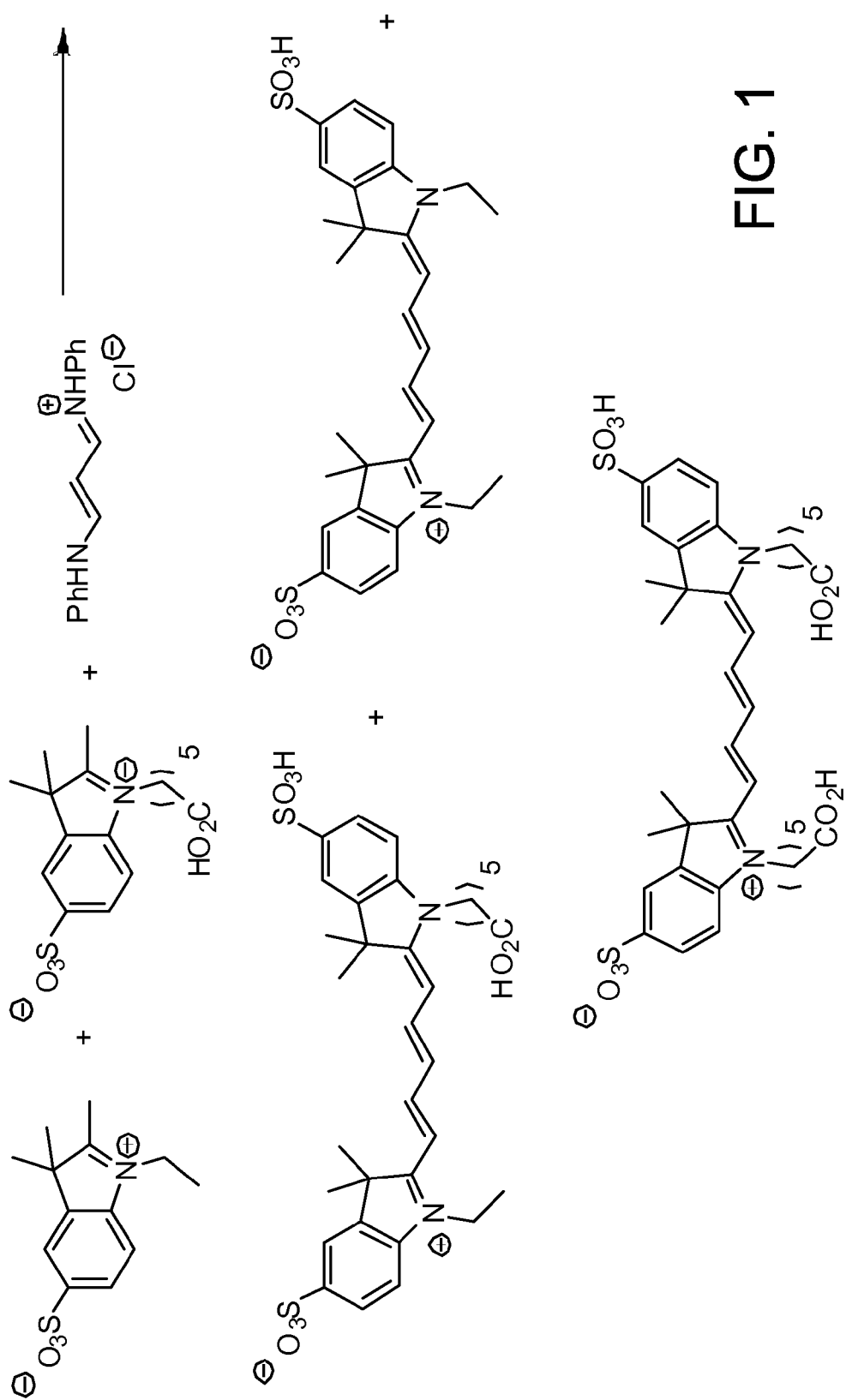
FIG. 1 shows a synthetic scheme for asymmetric dyes.

The present invention provides compositions and methods for the preparation of symmetric heptamethine carbocyanine dyes for both in vitro and in vivo imaging.

A facile and efficient synthetic route for the preparation of symmetric monofuctional carbocyanine dyes is developed herein. The one stage synthesis, giving symmetric functionalized dyes, minimizes the likelihood for formation of additional undesired dye side products, which are difficult to separate. This is in contrast to the more traditional synthesis of asymmetrically modified cyanine dyes, in which multiple unwanted dye side products may be generated. In addition to incorporation of carboxylic acid handles, this procedure is amenable to modification with azide and alkyne moieties, which are key components of the click reaction. The utility of these dyes for use in biolabeling experiments is expected to increase as the use of click chemistry becomes more prevalent in biotechnology.

The unique pathway for preparation of the malonaldehyde dianil intermediates described herein allows for facile introduction of a variety of functional groups onto the final cyanine dyes. By using different indoleninium and benzindolinium derivatives, this procedure can be applied to prepare not only Cy5 dyes but also their monofunctional Cy5.5 analogs, which, with red shifted absorption and emission profiles, are more suitable for biomedical imaging purposes. Accordingly, the invention provides a general strategy for synthesizing monofunctional carbocyanine derivatives that is amenable to the preparation of far-red/NIR cyanine dyes with high yields containing acid, alkyne, or azide synthetic handles. As shown in the examples below, these dyes have a variety of applications in bio- and bioorthogonal labeling schemes. Furthermore, using this synthetic approach, installation of additional useful functional groups such as amines, thiols, and maleimides is feasible.

The compounds described in this invention are useful in, e.g., fluorescence microscopy or flow cytometry. In addition, these compounds are useful as components in new small molecule, polymer, and nanoparticle-based probes for biological and biomedical imaging applications.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like.

As used herein, "alkynyl" refers to an alkyl group having one or more triple carbon-carbon bonds. Example alkynyl groups include ethynyl, propynyl, and the like.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "halo" or "halogen" includes fluoro, chloro, bromo, and iodo. The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

As used herein, the term "hydrazide" refers to a group characterized by a nitrogen to nitrogen covalent bond with four substituents with at least one of them being an acyl group, i.e. —(C=O)NH—N—N$_2$.

As used herein, the term "hydrazine" refers to a group with the formula —N$_2$H$_3$.

As used herein, the term "succinimidyl" refers to a group with the formula

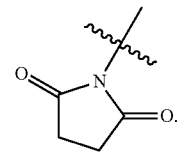 [SMILES: *N1C(=O)CCC1=O]

As used herein, the term "maleimide" refers to a group with the formula

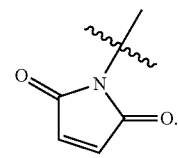 [SMILES: *N1C(=O)C=CC1=O]

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide—imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds of the invention, and pharmaceutically acceptable salts thereof, can be part of solvated or hydrated solid forms of the compound. These solvates and hydrates, as well as anhydrous and non-solvated forms, can occur in different solid forms such as amorphous forms as well as various crystalline forms.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Synthesis

Monofunctional dyes focused on symmetric carbocyanine scaffolds can be prepared using the synthetic pathway shown below in Scheme 1. These dyes have two identical monosulfonated-indoleninium moieties (4), and can be prepared in simple one-stage dye condensation reactions, which typically have significantly higher yields than reactions reported for asymmetric cyanine dye synthesis (Weissleder. *Nat. Biotechnol.* 2001, 10, 316; Leimgruber, A. B. C.; Cortez-Retamozo, V.; Etzrodt, M.; Newton, A. P.; Waterman P.; Figueiredo, J. L.; Kohler, R. H.; Elpek, N.; Mempel, T. R.; Swirski, F. K.; Nahrendorf, M.; Weissleder, R.; Pittet, M. J. *Neoplasia* 2009, 11). The two sulfonate groups on aromatic rings confer excellent water solubility to the final dyes. The acid, azide, and alkyne handles are introduced onto the central carbon atom of the polymethine chain through an alkyl chain followed by an arylamide linkage that is formed during the dye synthesis.

The desired functional groups can be incorporated into the malonaldehyde dianil intermediates (3a-c). These malonaldehyde dianil derivatives can be prepared via carboxylic acid intermediate, 2, which can be synthesized from methyl methyl 5,5-dimethoxyvalerate (1) via a Vilsmeier-Haack-Arnold aminoformylation followed by basic hydrolysis. An aniline moiety containing a carboxylic acid, alkyne, or azide in either the para- or meta-position can then be added to the reaction solution to yield the modified malonaldehyde dianil derivatives. Compounds 3a-c, which can be isolated as their chloride salts after acidic workup, are of sufficient purity for subsequent use in the dye condensation reactions.

Synthesis of the monofuctional carbocyanine fluorophores can be achieved by combining 1 equivalent of intermediate 3 and 4 equivalents of 1-ethyl-2,3,3-trimethylindoleninium-5-sulfonate (4) in acetic anhydride with 0.5% triethylamine. During the dye condensation, one of the two aniline groups undergoes an intramolecular nucleophilic attack, reacting with the carboxylic acid of the malonaldehyde derivative forming an amide bond. This unique intramolecular rearrangement can occur during the synthesis of all three dyes. The intramolecular rearrangement allows for facile installation of diverse functional groups onto the polymethine chain of the cyanine dye scaffold in a one stage reaction to provide a variety of cyanine dyes suitable for conjugation reactions.

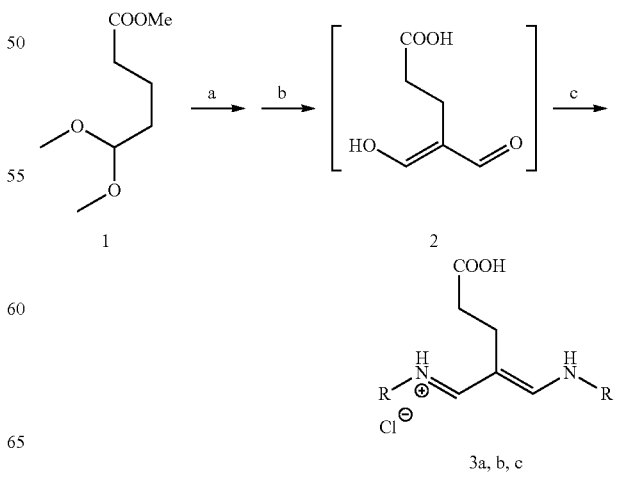

Scheme 1

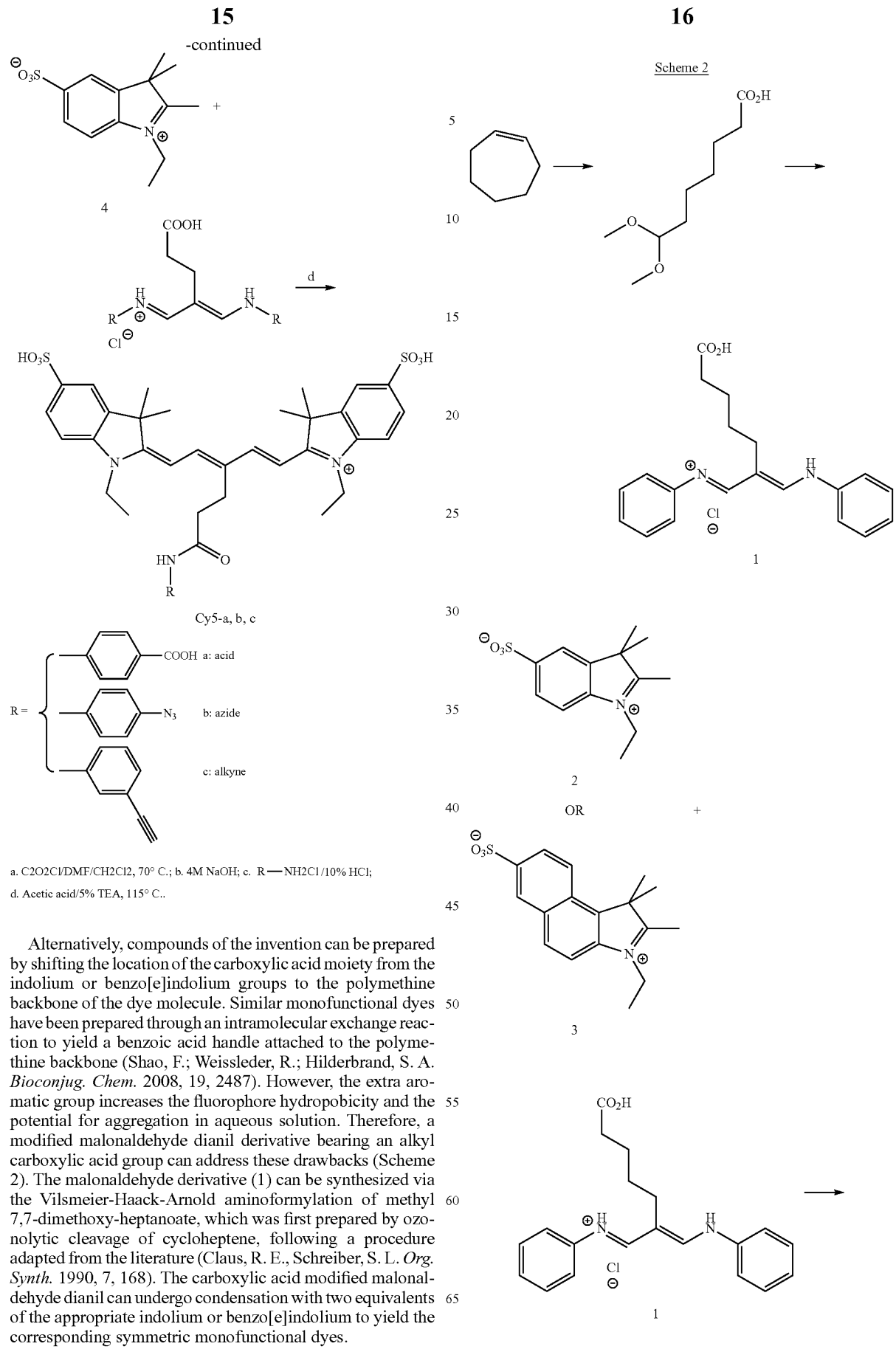

Alternatively, compounds of the invention can be prepared by shifting the location of the carboxylic acid moiety from the indolium or benzo[e]indolium groups to the polymethine backbone of the dye molecule. Similar monofunctional dyes have been prepared through an intramolecular exchange reaction to yield a benzoic acid handle attached to the polymethine backbone (Shao, F.; Weissleder, R.; Hilderbrand, S. A. Bioconjug. Chem. 2008, 19, 2487). However, the extra aromatic group increases the fluorophore hydropobicity and the potential for aggregation in aqueous solution. Therefore, a modified malonaldehyde dianil derivative bearing an alkyl carboxylic acid group can address these drawbacks (Scheme 2). The malonaldehyde derivative (1) can be synthesized via the Vilsmeier-Haack-Arnold aminoformylation of methyl 7,7-dimethoxy-heptanoate, which was first prepared by ozonolytic cleavage of cycloheptene, following a procedure adapted from the literature (Claus, R. E., Schreiber, S. L. *Org. Synth.* 1990, 7, 168). The carboxylic acid modified malonaldehyde dianil can undergo condensation with two equivalents of the appropriate indolium or benzo[e]indolium to yield the corresponding symmetric monofunctional dyes.

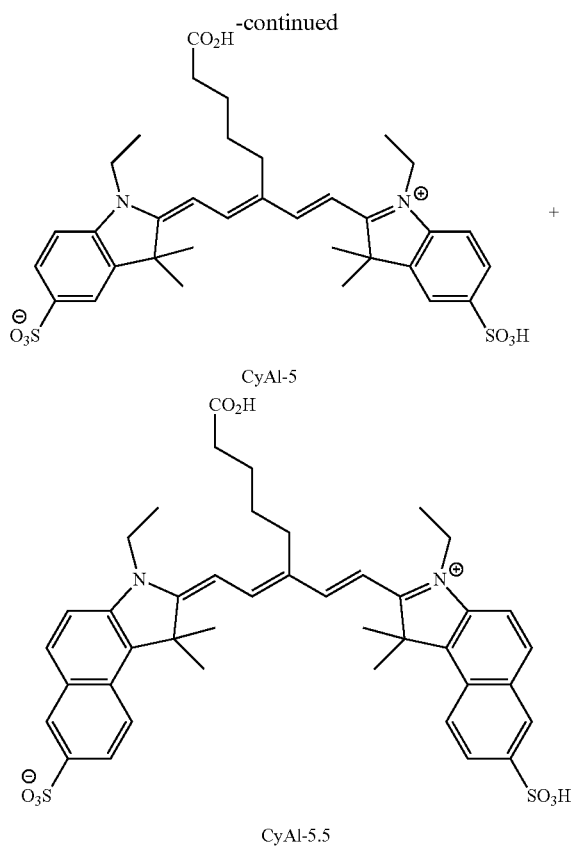

CyAl-5

CyAl-5.5

The synthesis of symmetric carbocyanine dyes often proceeds more smoothly and in higher yield than the corresponding asymmetric carbocyanines. This is in part due to the mixture of dye products that are generated in the preparation of the asymmetric dyes (FIG. 1). The symmetric, water-soluble alkyl-carboxylic acid derivatized dyes (CyAl-5 and CyAl-5.5) can be prepared by condensation of malonaldehyde dianil intermediate 1 with indolium 2 or benzo[e]indolium 3 using a mixture of acetic anhydride, acetic acid and triethylamine as solvent.

Compounds of the invention can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures, which can range from the solvent's freezing temperature to the solvent's boiling temperature at atmospheric pressure, or even higher temperatures if the reaction is carried out in a sealed reaction vessel. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Targeted Compounds for Optical Imaging

The compounds and compositions including asymmetric or symmetric monofunctional carbocyanine dyes as described herein are useful as far-red or near infrared (NIR) optical imaging agents in fluorescence-based imaging methods, e.g., for disease detection and diagnosis, therapeutic applications and for biochemical analysis, see, e.g., Weissleder et al., Nat. Biotechnol. 17:375-8 (1999); Weissleder et al., Nat. Med. 9:123-8 (2003), inter alia. The present invention provides improved bright far-red and near infrared, dyes that can be used in place of present NIR dyes, e.g., for conjugation to targeting agents, e.g., biomolecules (e.g., using the methods described in Ballou et al., Curr. Med. Chem. 12:795-805 (2005); Lin et al., Bioconjug. Chem. 13:605-10 (2002); Mujumdar et al., Bioconjug. Chem. 4:105-11 (1993); Mujumdar et al., Bioconjug. Chem. 7:356-62 (1996); Narayana and Patonay, J. Org. Chem. 60:2391-2395 (1995)), a variety biological/biomedical macromolecules, and surface-modified nanoparticles (see, e.g., Pham et al., Bioconjug. Chem. 16:735-40 (2005); McCarthy et al., Nanomed. 2:153-67 (2007)). The improved bright far-red and near infrared dyes described herein can be used, for example, for attachment to targeting agents such as antibodies, antibody fragments, peptides, small molecules, DNA, RNA, aptamers, nanoparticles, biopolymers, and the like. In some embodiments, the targeting agent is or also includes a therapeutic agent, e.g., as described in PCT/US2009/062958. Although these fluorescent dyes are preferably water-soluble, derivatives that are only soluble in organic solvents are not excluded.

A targeting agent can be any compound, such as a small molecule or biomolecule (e.g., an antibody or antigen-binding fragment thereof), that binds specifically to a selected target, and can be functionalized by the addition of a diene or dienophile optionally via a linker.

Antibodies

The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments, which retain the ability to bind antigen. Such fragments can be obtained commercially, or using methods known in the art. For example F(ab)2 fragments can be generated by treating the antibody with an enzyme such as pepsin, a non-specific endopeptidase that normally produces one F(ab)2 fragment and numerous small peptides of the Fc portion. The resulting F(ab)2 fragment is composed of two disulfide-connected Fab units. The Fc fragment is extensively degraded and can be separated from the F(ab)2 by dialysis, gel filtration or ion exchange chromatography. F(ab) fragments can be generated using papain, a non-specific thiol-endopeptidase that digests IgG molecules, in the presence of a reducing agent, into three fragments of similar size: two Fab fragments and one Fc fragment. When Fc fragments are of interest, papain is the enzyme of choice because it yields a 50.00 Dalton Fc fragment; to isolate the F(ab) fragments, the Fc fragments can be removed, e.g., by affinity purification using protein A/G. A number of kits are available commercially for generating F(ab) fragments, including the ImmunoPure IgG1 Fab and F(ab')$_2$ Preparation Kit (Pierce Biotechnology, Rockford, Ill.). In addition, commercially available services for generating antigen-binding fragments can be used, e.g., BioExpress, West Lebanon, N.H.

The antibody can be a polyclonal, monoclonal, recombinant, e.g., a chimeric, de-immunized or humanized, fully human, non-human, e.g., murine, or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region.

In addition to utilizing whole antibodies, the invention encompasses the use of binding portions of such antibodies. Such binding portions include Fab fragments, F(ab')2 fragments, and Fv fragments. These antibody fragments can be made by conventional procedures, such as proteolytic fragmentation procedures, as described in J. Goding, *Monoclonal Antibodies: Principles and Practice*, pp. 98-118 (N.Y. Academic Press 1983).

Chimeric, humanized, de-immunized, or completely human antibodies are desirable for applications which include repeated administration, e.g., therapeutic treatment of human subjects.

The antibody can also be a single chain antibody. A single-chain antibody (scFV) can be engineered (see, for example, Colcher et al., Ann. N. Y. Acad. Sci. 880:263-80 (1999); and Reiter, Clin. Cancer Res. 2:245-52 (1996)). The single chain antibody can be dimerized or multimerized to generate multivalent antibodies having specificities for different epitopes of the same target protein. In some embodiments, the antibody is monovalent, e.g., as described in Abbs et al., Ther. Immunol. 1(6):325-31 (1994), incorporated herein by reference.

Methods for making suitable antibodies are known in the art. See, e.g., E. Harlow, et. al., editors, Antibodies: A Laboratory Manual (1988).

In some embodiments, the antibody binds specifically to a tumor antigen, or to an antigen present in a tissue in which a tumor is present. A number of antibodies against cancer-related antigens are known (Ross et al., Am J Clin Pathol 119(4):472-485, 2003). Examples include Alemtuzumab (Campath); Daclizumab (Zenapax); Rituximab (Rituxan); Trastuzumab (Herceptin); Gemtuzumab (Mylotarg); Ibritumomab (Zevalin); Edrecolomab (Panorex); Tositumomab (Bexxar); CeaVac; Epratuzumab (LymphoCide); Mitumomab; Bevacizumab (Avastin); Cetuximab (C-225; Erbitux); Edrecolomab; Lintuzumab (Zamyl); MDX-210; IGN-101; MDX-010; MAb, AME; ABX-EGF; EMD 72 000; Apolizumab; Labetuzumab; ior-t1; MDX-220; MRA; H-11 scFv; Oregovomab; huJ591 MAb, BZL; Visilizumab; TriGem; TriAb; R3; MT-201; G-250, unconjugated; ACA-125; Onyvax-105; CDP-860; BrevaRex MAb; AR54; IMC-1C11; GlioMAb-H; ING-1; Anti-LCG MAbs; MT-103; KSB-303; Therex; KW-2871; Anti-HMI.24; Anti-PTHrP; 2C4 antibody; SGN-30; TRAIL-RI MAb, CAT; H22xKi-4; ABX-MA1; Imuteran; and Monopharm-C. In some embodiments in which the targeting agent is specific for a tumor antigen or cancerous tissue, the payload can be a therapeutic agent such as a cytotoxin, radioactive agent, or other therapeutic agent useful in treating cancer.

Small Molecules and Biomolecules

Small molecules are low molecular weight organic compounds (less than 2000 Daltons). Small molecules useful in the compositions and methods described herein bind with high affinity to a biopolymer, such as protein, nucleic acid, or polysaccharide, or other biological target. Useful small molecules are capable of being functionalized with a dienophile or a diene. For example, a small molecule can be an agent such as taxol, which binds specifically to microtubules and is capable of being functionalized with a dienophile such as trans-cyclooctene or another alkene. Other examples include small molecules that bind specifically to receptors for hormones, cytokines, chemokines, or other signaling molecules.

Biomolecules are organic molecules produced by living organisms, including large polymeric molecules such as proteins, polysaccharides, and nucleic acids as well as small molecules such as primary metabolites, secondary metabolites, and natural products. Specific small molecule examples include, but are not limited to, estradiol, testosterone, cholesterol, phosphatidylserine, or phosphatidylcholine.

Methods of Use

The compounds and compositions described herein can be used in both in vitro and in vivo imaging methods known in the art, e.g., as described in US 2005/0249668. General principles of fluorescence, optical image acquisition, and image processing can be applied in the practice of the invention. For a review of optical imaging techniques, see, e.g., Alfano et al., Ann. NY Acad. Sci., 820:248-270, 1997. Imaging systems typically include three basic components: (1) a near infrared light source, (2) an apparatus for separating or distinguishing emissions from light used for chromophore excitation, and (3) a detection system.

The light source provides monochromatic (or substantially monochromatic) near infrared light. The light source can be a suitably filtered white light, e.g., bandpass light from a broadband source. For example, light from a 150-watt halogen lamp can be passed through a suitable bandpass filter commercially available from Omega Optical (Brattleboro, Vt.). In some embodiments, the light source is a laser. See, e.g., Boas et al., Proc. Natl. Acad. Sci. USA 91:4887-4891, 1994; Ntziachristos et al., Proc. Natl. Acad. Sci. USA 97:2767-2772, 2000; Alexander, J. Clin. Laser Med. Surg. 9:416-418, 1991. Information on near infrared lasers for imaging can also be found on the Internet (e.g., at imds.com) and various other well-known sources.

A high pass or bandpass filter (650 nm) can be used to separate optical emissions from excitation light. A suitable high pass or bandpass filter is commercially available from Omega Optical. In some embodiments, a single excitation wavelength can be used to excite multiple different fluorochromes on a single probe or multiple probes (with different activation sites), and spectral separation with a series of bandpass filters, diffraction grating, or other means can be used to independently read the different activations.

In general, the light detection system can include light-gathering/image-forming and light-detection/image-recording components. Although the light-detection system can be a single integrated device that incorporates both components, the light-gathering/image-forming and light-detection/image-recording components will be discussed separately. However, a recording device may simply record a single (time varying) scalar intensity instead of an image. For example, a catheter-based recording device can record information from multiple sites simultaneously (i.e., an image), or can report a scalar signal intensity that is correlated with location by other means (such as a radio-opaque marker at the catheter tip, viewed by fluoroscopy).

A particularly useful light-gathering/image-forming component is an endoscope. Endoscopic devices and techniques that have been used for in vivo optical imaging of numerous tissues and organs, including peritoneum (Gahlen et al., J. Photochem. Photobiol. B 52:131-135, 1999), ovarian cancer (Major et al., Gynecol. Oncol. 66:122-132, 1997), colon (Mycek et al., Gastrointest. Endosc. 48:390-394, 1998; Stepp et al., Endoscopy 30:379-386, 1998) bile ducts (Izuishi et al., Hepatogastroenterology 46:804-807, 1999), stomach (Abe et al., Endoscopy 32:281-286, 2000), bladder (Kriemair et al., Urol. Int. 63:27-31, 1999; Riedl et al., J., Endourol. 13:755-759, 1999), and brain (Ward, J. Laser Appl. 10:224-228, 1998) can be employed in the practice of the present invention. Other types of light gathering components useful in the methods described herein are catheter-based devices, including fiber optic devices. Such devices are particularly suitable for intravascular imaging. See, e.g., Tearney et al., Science 276:2037-2039, 1997; Boppart et al., Proc. Natl. Acad. Sci. USA 94:4256-4261, 1997.

Still other imaging technologies, including phased array technology (Boas et al., Proc. Natl. Acad. Sci. USA 91:48874891, 1994; Chance, Ann. NY Acad. Sci. 838:29-45, 1998), diffuse optical tomography (Cheng et al., Optics Express 3:118-123, 1998; Siegel et al., Optics Express 4:287-298, 1999), intravital microscopy (Dellian et al., Br. J. Cancer 82:1513-1518,2000; Monsky et al, Cancer Res. 59:4129-4135, 1999; Fukumura et al., Cell 94:715-725, 1998), fluorescence molecular tomography (FMT), fluorescence reflectance imaging (FRI), and confocal imaging (Korlach et al., Proc. Natl. Acad. Sci. USA 96:8461-8466, 1999; Rajadhyaksha et al., J. Invest. Dermatol. 104:946-952, 1995; Gonzalez et al., J. Med. 30:337-356, 1999) can be employed in the practice of the present methods.

Any suitable light-detection/image-recording component, e.g., charge-coupled device (CCD) systems or photographic film, can be used. The choice of light-detection/image-recording component will depend on factors including type of light gathering/image forming component being used. Selecting suitable components, assembling them into a near infrared imaging system, and operating the system is within the ability of a person of ordinary skill in the art.

In addition, the compositions and methods of the present invention can be used in combination with other imaging compositions and methods. For example, the agents of the present invention can be imaged by NIR imaging methods either alone or in combination with other traditional imaging modalities, such as, X-ray, computed tomography (CT), MR imaging, ultrasound, positron emission tomography (PET), and single photon computerized tomography (SPECT). For instance, the methods described herein can be used in combination with CT or MRI to obtain both anatomical and molecular information simultaneously, for example, by co-registration of with an image generated by another imaging modality. The compositions and methods of the present invention can also be used in combination with X-ray, CT, PET, ultrasound, SPECT and other optical and MR contrast agents or alternatively, the agents of the present invention may also include imaging agents, such as iodine, gadolinium atoms and radioactive isotopes, which can be detected using CT, PET, SPECT, and MR imaging modalities in combination with optical imaging. The imaging agents can be linked to or incorporated in the agents.

In Vivo Imaging

The present compounds and compositions can be used in in vivo imaging methods. In general, such methods include administering to a subject one or more compounds or compositions described herein; optionally allowing the agent(s) to distribute within the subject; exposing the subject to light of a wavelength absorbable by at least one fluorophore in the imaging agent; and detecting an optical signal emitted by the fluorophore. The emitted optical signal can be used to construct an image. The image can be a tomographic image. Furthermore, it is understood that the methods (or portions thereof) can be repeated at intervals to evaluate the subject over time.

The illuminating and/or detecting steps can be performed using any device or apparatus known in the art, e.g., an endoscope, catheter, tomographic system, planar system, hand-held imaging system, goggles, or an intraoperative imaging system or microscope.

Before or during these steps, a detection system can be positioned around or in the vicinity of a subject (for example, an animal or a human) to detect signals emitted from the subject. The emitted signals can be processed to construct an image, for example, a tomographic image. In addition, the processed signals can be displayed as images either alone or as combined images.

In addition, it is possible to practice an in vivo imaging method that selectively detects and images one or more molecular imaging probes, including the imaging agents simultaneously. In these embodiments, two or more imaging probes whose signal properties are distinguishable from one another are administered to the subject, either at the same time or sequentially, wherein at least one of the molecular imaging probes is a agent. The use of multiple probes permits the recording of multiple biological processes, functions or targets.

The subject may be a vertebrate, for example, a mammal, for example, a human. The subject may also be a non-vertebrate (for example, *C. elegans, drosophila*, or another model research organism, etc.) used in laboratory research.

Information provided by such in vivo imaging approaches, for example, the presence, absence, or level of emitted signal can be used to detect and/or monitor a disease in the subject. Exemplary diseases include, without limitation, autoimmune disease, bone disease, cancer, cardiovascular disease, environmental disease, dermatological disease, immunologic disease, inherited disease, infectious disease, metabolic disease, neurodegenerative disease, ophthalmic disease, and respiratory disease. In addition, in vivo imaging can be used to assess the effect of a compound or therapy by using the imaging agents, wherein the subject is imaged prior to and after treatment with the compound or therapy, and the corresponding signal/images are compared.

The invention also features an in vivo imaging method where labeled cells are administered to the recipient. The cells can be labeled with the imaging agents ex vivo. The cells can be derived directly from a subject or from another source (e.g., from another subject, cell culture, etc.). The imaging agents can be mixed with the cells to effectively label the cells and the resulting labeled cells administered to the subject into a subject in step (a). Steps (b)-(d) then are followed as described above. This method can be used for monitoring trafficking and localization of certain cell types, including T-cells, tumor cells, immune cells and stem cells, and other cell types. In particular, this method may be used to monitor cell-based therapies.

The methods described herein can be used to determine a number of indicia, including tracking the localization of the agent in the subject over time or assessing changes or alterations in the metabolism and/or excretion of the agent in the subject over time. The methods can also be used to follow therapy for such diseases by imaging molecular events and biological pathways modulated by such therapy, including but not limited to determining efficacy, optimal timing, optimal dosing levels (including for individual patients or test subjects), and synergistic effects of combinations of therapy.

The methods and compositions described herein can be used to help a physician or surgeon to identify and characterize areas of disease, such as arthritis, cancers and specifically colon polyps, or vulnerable or unstable plaque, atherosclerosis, to distinguish diseased and normal tissue, such as detecting tumor margins that are difficult to detect using an ordinary operating microscope, e.g., in brain surgery, to help dictate a therapeutic or surgical intervention, e.g., by determining whether a lesion is cancerous and should be removed or non-cancerous and left alone, or in surgically staging a disease, e.g., intraoperative lymph node staging, sentinel lymph node mapping, or assessing intraoperative bleeding.

The methods and compositions described herein can also be used in the detection, characterization and/or determination of the localization of a disease, especially early disease, the severity of a disease or a disease-associated condition, the staging of a disease, and/or monitoring a disease. The presence, absence, or level of an emitted signal can be indicative of a disease state.

The methods and compositions disclosed herein can also be used to monitor and/or guide various therapeutic interventions, such as surgical procedures, and monitoring drug therapy, including cell based therapies. The methods can also be used in prognosis of a disease or disease condition.

With respect to each of the foregoing, examples of such disease or disease conditions that can be detected or monitored (before, during or after therapy) include inflammation (for example, inflammation caused by arthritis, for example, rheumatoid arthritis), cancer (for example, colorectal, ovarian, lung, breast, prostate, cervical, testicular, skin, brain, gastrointestinal, pancreatic, liver, kidney, bladder, stomach, leukemia, mouth, esophageal, bone), cardiovascular disease (for example, atherosclerosis and inflammatory conditions of blood vessels, ischemia, hypertension, stroke, thrombosis, disseminated intravascular coagulation), dermatologic disease (for example, Kaposi's Sarcoma, psoriasis, allergic dermatitis), ophthalmic disease (for example, macular degeneration, diabetic retinopathy), infectious disease (for example, bacterial, viral, fungal and parasitic infections, including Acquired Immunodeficiency Syndrome, Malaria, Chagas Disease, Schistosomiasis), immunologic disease (for example, an autoimmune disorder, lymphoma, multiple sclerosis, rheumatoid arthritis, diabetes mellitus, lupus erythematosis, myasthenia gravis, Graves disease), central nervous system disease (for example, a neurodegenerative disease, such as Parkinson's disease or Alzheimer's disease, Huntington's Disease, amyotrophic lateral sclerosis, prion disease), inherited diseases, metabolic diseases, environmental diseases (for example, lead, mercury and radioactive poisoning, skin cancer), bone-related disease (for example, osteoporosis, primary and metastatic bone tumors, osteoarthritis), neurodegenerative disease, and surgery-related complications (such as graft rejection, organ rejection, alterations in wound healing, fibrosis or other complications related to surgical implants).

The methods and compositions described herein, therefore, can be used, for example, to determine the presence and/or localization of tumor cells, the presence and/or localization of inflammation, including the presence of activated macrophages, for instance in atherosclerosis or arthritis, the presence and in localization of vascular disease including areas at risk for acute occlusion (i.e., vulnerable plaques) in coronary and peripheral arteries, regions of expanding aneurysms, unstable plaque in carotid arteries, and ischemic areas.

The methods and compositions described herein, can also be used in identification and evaluation of cell death, injury, apoptosis, necrosis, hypoxia and angiogenesis. The methods and compositions can also be used for drug delivery and to monitor drug delivery, especially when drugs or drug-like molecules are chemically attached to the imaging agents.

In Vitro Imaging

With respect to in vitro imaging methods, the compounds and compositions described herein can be used in a variety of in vitro assays. An exemplary in vitro imaging method comprises: contacting a sample, for example, a biological sample, with one or more imaging agents of the invention; allowing the agent(s) to interact with a biological target in the sample; optionally, removing unbound agents; illuminating the sample with light of a wavelength absorbable by a fluorophore of the agents; and detecting a signal emitted from fluorophore thereby to determine whether the agent has been activated by or bound to the biological target.

After an agent has been designed, synthesized, and optionally formulated, it can be tested in vitro by one skilled in the art to assess its biological and performance characteristics. For instance, different types of cells grown in culture can be used to assess the biological and performance characteristics of the agent. Cellular uptake, binding or cellular localization of the agent can be assessed using techniques known in the art, including, for example, fluorescent microscopy, FACS analysis, immunohistochemistry, immunoprecipitation, in situ hybridization and fluorescence resonance energy transfer (FRET). By way of example, the agents can be contacted with a sample for a period of time and then washed to remove any free agents. The sample can then be viewed using an appropriate detection device such as a fluorescent microscope equipped with appropriate filters matched to the optical properties of a fluorescent agent. Fluorescence microscopy of cells in culture or scintillation counting is also a convenient means for determining whether uptake and binding has occurred. Tissues, tissue sections and other types of samples such as cytospin samples can also be used in a similar manner to assess the biological and performance characteristics of the agents. Other detection methods including, but not limited to flow cytometry, immunoassays, hybridization assays, and microarray analysis can also be used.

Compositions

The compounds described herein can be provided dry or dissolved in a carrier or vehicle, e.g., pharmaceutically acceptable carriers and vehicles. Useful carriers and vehicles include, but are not limited to, ion exchangers, alumina, aluminum stearate, lecithin, serum proteins such as albumin, buffer substances such as phosphate, glycine, sorbic acid, potassium sorbate, tris(hydroxymethyl)amino methane ("TRIS"), partial glyceride mixtures of fatty acids, water, salts or electrolytes, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polypropylene block co-polymers, sugars such as glucose, and suitable cryoprotectants.

The compounds and compositions can be administered in the form of a sterile injectable preparation. This preparation can be prepared by those skilled in the art of such preparations according to techniques known in the art. The possible vehicles or solvents that can be used to make injectable preparations include water, Ringer's solution, and isotonic sodium chloride solution, and 5% D-glucose solution (D5W). In addition, oils such as mono- or di-glycerides and fatty acids such as oleic acid and its derivatives can be used. The compounds and compositions can be administered orally, parenterally, by inhalation, topically, rectally, nasally, buccally, vaginally, or via an implanted reservoir. The term "parenteral administration" includes intravenous, intramuscular, intra-articular, intrasynovial, intrasternal, intrathecal, intraperitoneal, intracisternal, intrahepatic, intralesional, and intracranial injection or infusion techniques. The probes can also be administered via catheters or through a needle to any tissue.

For ophthalmic use, the compounds and compositions can be formulated as micronized suspensions in isotonic, pH-adjusted, sterile saline. Alternatively, the compounds and compositions can be formulated in ointments such as petrolatum.

For topical application, the compounds and compositions can be formulated in a suitable ointment, such as petrolatum. Transdermal patches can also be used. Topical application for the lower intestinal tract or vagina can be achieved by a suppository formulation or enema formulation.

The formulation of the compounds and compositions can also include an antioxidant or some other chemical compound that prevents or reduces the degradation of the baseline fluorescence, or preserves the fluorescence properties, including, but not limited to, quantum yield, fluorescence lifetime, and excitation and emission wavelengths. These antioxidants or other chemical compounds can include, but are not limited to, melatonin, dithiothreitol (dTT), defroxamine (DFX), methionine, and N-acetyl cysteine.

Dosing of the new chromophores and probes will depend on a number of factors including the instruments' sensitivity, as well as a number of subject-related variables, including animal species, age, body weight, mode of administration, sex, diet, time of administration, and rate of excretion.

Prior to use of the invention or any pharmaceutical composition of the invention, the subject can be treated with an agent or regimen to enhance the imaging process. For example, a subject can be put on a special diet prior to imaging to reduce any auto-fluorescence or interference from ingested food, such as a low pheophorbide diet to reduce interference from fluorescent pheophorbides that are derived from some foods, such as green vegetables. Alternatively, a cleansing regimen can be used prior to imaging, such as those cleansing regimens that are used prior to colonoscopies and include use of agents such as Visiciol. The subject (patient or animal) can also be treated with pharmacological modifiers to improve image quality. For example, using low dose enzymatic inhibitors to decrease background signal relative to target signal (secondary to proportionally lowering enzymatic activity of already low-enzymatic activity normal tissues to a greater extent than enzymatically-active pathological tissues) can improve the target-to-background ratio during disease screening. As another non-limiting example, pretreatment with methotrexate to relatively increase uptake in abnormal tissue (i.e., metabolically active cancers) in conjunction with folate-based targeted delivery can be employed.

EXAMPLES

The invention is further described in the following examples, which are not intended to limit the scope of the invention described in the claims.

Example 1

Synthesis of Symmetric Carbocyanine Dyes and their Use in Bio-Orthogonal Conjugation and Fluorescence Cell Imaging All chemicals were purchased from Aldrich or TCI and were used as received. All of the solvents were at least of reagent grade and were used without further purification. All of the dyes for characterization were purified by high-performance liquid chromatography (HPLC) on a Varian 210 instrument equipped with a 335 diode array detector. If not otherwise noted, HPLC buffer A is 0.1% trifluoroacetic acid in water and buffer B was 90% acetonitrile in buffer A. $^1$H (400 MHz) and $^{13}$C NMR (100 MHz) spectra were collected on a Bruker Advance-400 NMR spectrometer at ambient temperature. The chemical shifts were measured versus tetramethylsilane (TMS) as an internal standard. High-resolution electrospray ionization (ESI) mass spectra were obtained on a Bruker Daltonics APEXIV 4.7 Tesla Fourier Transform Ion Cyclotron Resonance Mass Spectrometer (FT-ICR-MS).

Synthesis of 5-(phenylamino)-4-(phenylimino)methyl)-4-pentenoic acid derivatives (Intermediates 3a-c)

General synthetic route. Anhydrous dimethylformamide (1.01 mL, 13 mmole) and oxalyl chloride (1.26 g, 10 mmole) were added sequentially into 30 mL anhydrous dichloromethane (DCM) in an acetone/dry ice bath. The mixture was allowed to warm to room temperature over 15 minutes. Methyl 5,5-dimethoxyvalerate (881 mg, 5 mmole) was then added dropwise to the reaction solution followed by heating at 70° C. for 2 hours, allowing the DCM to evaporate. The resulting yellowish oil was dissolved in 5 mL of 4 M NaOH and was heated at 70° C. for 1 hour. Before their use, the anilines (4-aminobenzoic acid, 4-azidoaniline, 3-ethynylaniline) were converted to their corresponding chloride salts on a 10 mmol scale by dissolving the aniline in acetone and precipitating its salt by addition of excess concentrated aqueous HCl. After removing the solvent under vacuum, the appropriate aniline chloride salt (10 mmol), dissolved in 5 mL water, was added to the basic, crude reaction solution and was allowed to stir at room temperature for 1 or more hours, until the reaction was complete. The final malonaldehyde dianil hydrochloride salts were precipitated as light yellow solids after the addition of 5 mL of 10% aqueous HCl and were collected by filtration. The products were above 95% pure and used directly in the dye synthesis without further purification if not mentioned specifically.

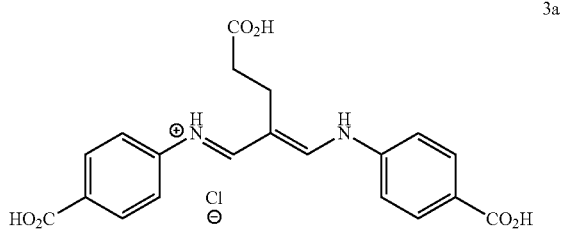

Carboxylic Acid Intermediate (3a)

Yield 65%, 1.22 g. $^1$H NMR (400 MHz, DMSO-$d_6$): δ 11.65 (b, 2H), 8.80 (s, 2H), 8.08 (d, 4H, J=8.8 Hz), 7.63 (d, 4H, J=8.8 Hz), 2.90 (t, 2H, J=7.6 Hz), 2.48 (t, 2H, J=7.9 Hz). $^{13}$C NMR (400 MHz, DMSO-$d_6$): δ 174.78, 167.50, 160.44, 143.41, 131.97, 128.74, 119.31 112.49, 32.75, 18.35. HRMS-ESI [M+H]$^+$ m/z calcd. for [$C_{20}H_{18}N_2O_6$]$^-$ 383.1238, found 383.1231.

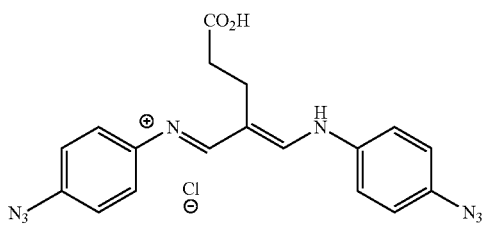

Azide Intermediate (3b)

4-Azidoaniline hydrochloride was used as received. Yield 61%, 1.24 g. $^1$H NMR (400 MHz, DMSO-$d_6$): δ 8.85 (s, 2H), 7.65 (d, 4H, J=8.8 Hz), 7.22 (d, 4H, J=8.7 Hz), 6.82 (d, 1H, J=8.4 Hz), 6.68 (d, 1H, J=8.5 Hz), 2.91 (t, 2H, J=7.3 Hz), 2.45 (t, 2H, J=7.8 Hz). $^{13}$C NMR (400 MHz, DMSO-$d_6$): δ 173.84, 158.22, 145.09, 136.89, 136.44, 127.16, 120.35, 119.93, 115.91, 109.97, 32.72, 19.10. HRMS-ESI [M+H]$^+$ m/z calcd. for $[C_{18}H_{16}N_8O_2]^+$ 377.1469, found 377.1473.

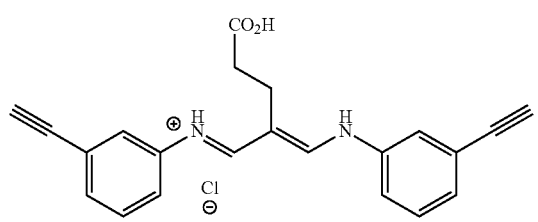

Alkyne Intermediate (3c)

Crude precipitates were purified on a silica column starting from 5% MeOH/DCM. The pure product was eluted at 15% MeOH/DCM. Yield 24%, 440 mg. $^1$H NMR (400 MHz, DMSO-$d_6$): δ 8.18 (s, 2H), 7.39 (s, 2H), 7.35 (d, 2H, J=7.2 Hz), 7.32 (d, 2H, J=1.5 Hz), 7.18 (d, 2H, J=7.0), 4.24 (s, 2H), 2.79 (t, 2H, J=7.5 Hz), 2.44 (t, 2H, J=7.8 Hz). $^{13}$C NMR (400 MHz, DMSO-$d_6$): δ 175.02, 155.59, 145.80, 130.38, 127.38, 123.30, 121.25, 119.73, 113.94, 83.81, 81.57, 32.72, 19.10. HRMS-ESI [M+H]$^+$ m/z calcd. for $[C_{22}H_{18}N_2O_2]^+$ 343.1441, found 343.1443.

Figure 2A:
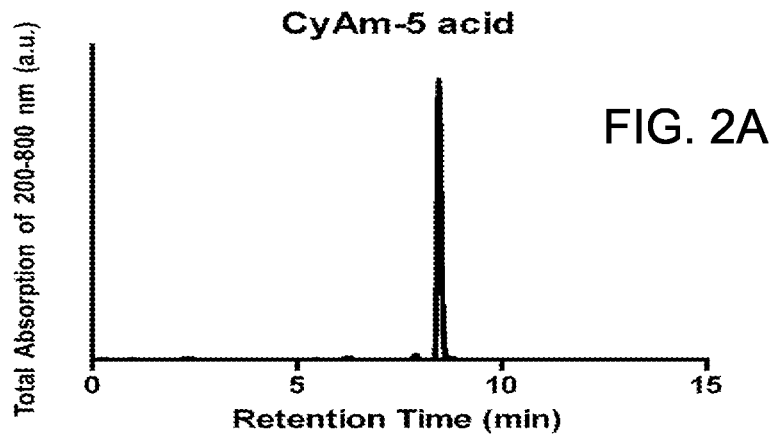
FIG. 2A-C shows HPLC traces indicating the purity of the Cy5 analogues. (A) CyAm-5 acid; (B) CyAm-5 azide; (C) CyAm-5 alkyne.
Figure 2B:
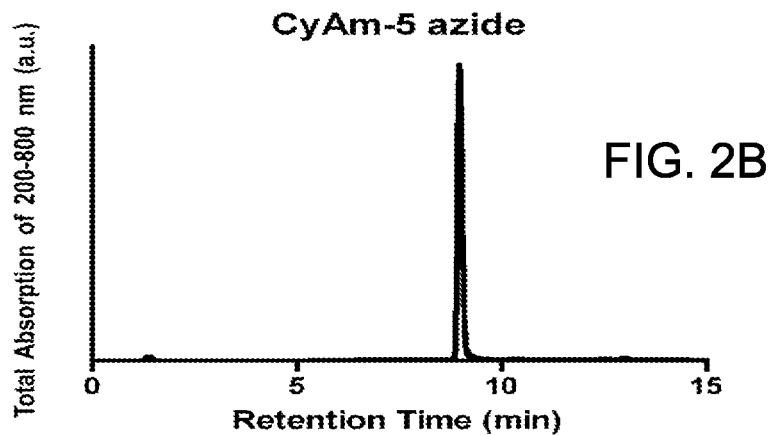
Figure 2C:
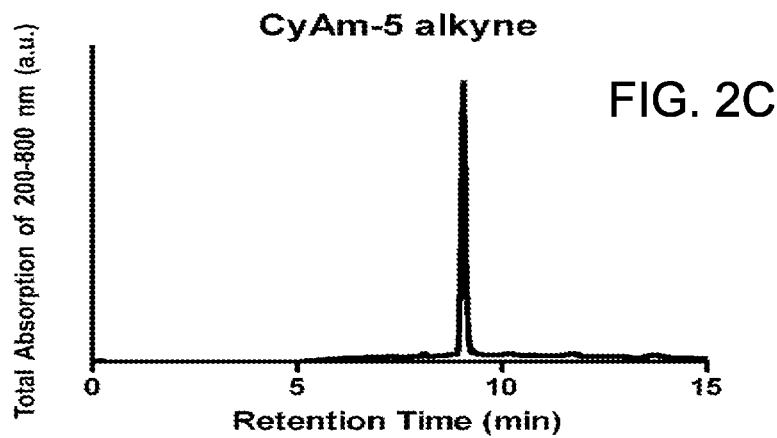

Dye Synthesis (CyAm-5 acid, CyAm-5 azide and CyAm-5 alkyne). General Synthetic Route 1-Ethyl-2,3,3-trimethylindoleninium-5-sulfonate (4) was prepared according to literature procedures (5). Indoleninium 4 (4 equiv.) and intermediates 3 (1 equiv.) were dissolved in 5 mL acetic anhydride with 0.5% v/v triethylamine. The reaction solution was heated at 115° C. for 1 hour in a sealed flask. The product crude was then precipitated by the addition of diethyl ether and was washed with copious amount of diethylether afterwards. Preparative HPLC (Varian Pursuit XRs 10 C18 250×21.2 mm column, 0-25% buffer B over 30 minutes at a flow rate of 21 mL/min) was applied to purify CyAm-5 acid giving the blue dye as the free acid. The other dyes (CyAm-5 azide and CyAm-5 alkyne) were isolated as their ammonium salts by preparative HPLC over the same gradient but with buffer A as 50 mM NH$_4$OAc, pH 7.0 and buffer B as acetonitrile. FIG. 2 shows the HPLC traces indicating the purity of CyAm-5 acid, CyAm-5 azide, and CyAm-5 alkyne.

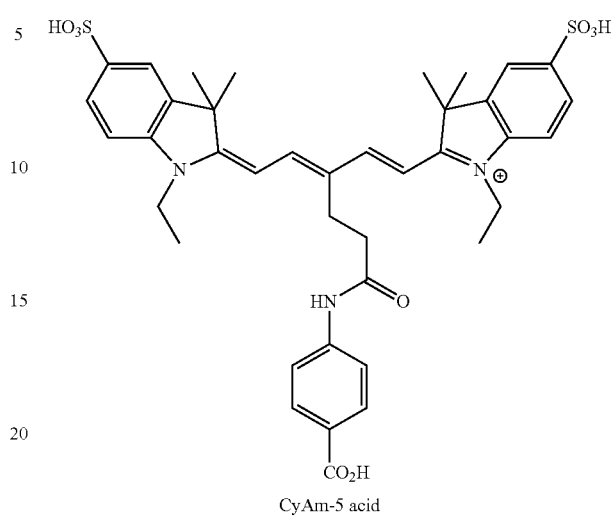

CyAm-5 acid

CyAm-5 Acid (5a)

Yield 66%, 252 mg starting with 0.5 mmole of 3a. $^1$H NMR (400 MHz, DMSO-$d_6$): δ 10.30 (s, 1H), 8.21 (d, 2H, J=14.1 Hz), 7.86 (d, 2H, J=8.7 Hz), 7.84 (s, 2H), 7.72 (d, 2H, J=8.8 Hz), 7.66 (d, 2H, J=8.2 Hz), 7.35 (d, 2H, J=8.4 Hz), 6.33 (d, 2H, J=14.2 Hz), 4.21 (m, 4H), 2.99 (t, 2H, J=6.7 Hz), 2.60 (t, 2H, J=7.1 Hz), 1.71 (s, 12H), 1.30 (t, 6H, J=7.1 Hz). $^{13}$C NMR (400 MHz, DMSO-$d_6$): δ 173.43, 172.03, 167.51, 154.11, 145.75, 143.81, 142.19, 141.40, 133.99, 130.99, 126.73, 125.62, 120.61, 118.98, 110.63, 100.36, 49.61, 39.67, 36.10, 27.46, 20.58, 12.69. HRMS-ESI [M]$^+$ m/z calcd. for $[C_{39}H_{44}N_3O_9S_2]^+$ 762.2513, found 762.2539.

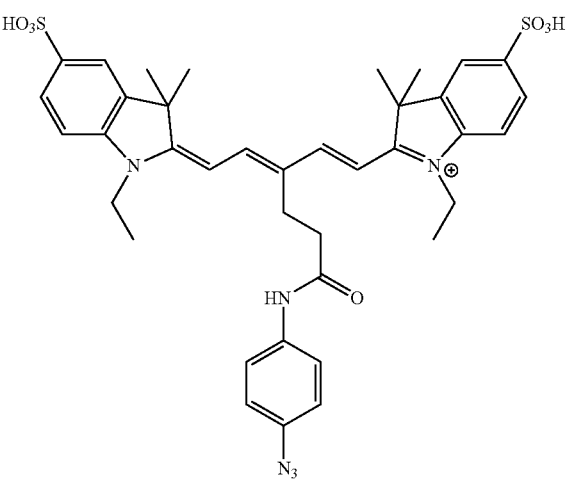

CyAm-5 azide

CyAm-5 Azide (5b)

Yield: 64%, 116 mg starting with 0.24 mmole of 3b. $^1$H NMR (400 MHz, DMSO-$d_6$): δ 10.08 (s, 1H), 8.20 (d, 2H, J=14.2 Hz), 7.83 (s, 2H), 7.66 (d, 2H, J=8.9 Hz), 7.64 (d, 2H, J=8.7 Hz), 7.34 (d, 2H, J=8.4 Hz), 7.03 (d, 2H, J=8.9 Hz), 6.32 (d, 2H, J=14.2 Hz), 4.20 (m, 4H), 2.98 (t, 2H, J=6.7 Hz), 2.54 (t, 2H, J=6.8 Hz), 1.70 (s, 12H), 1.29 (t, 6H, J=7.1 Hz). $^{13}$C NMR (400 MHz, DMSO-$d_6$): δ 173.73, 171.74, 154.46, 146.15, 142.49, 141.71, 137.42, 134.65, 133.61, 17.05, 121.55, 120.94, 120.31, 110.93, 100.73, 49.91, 39.63, 36.23, 27.79, 21.04, 13.02. HRMS-ESI [M]$^+$ m/z calcd. for [$C_{38}H_{43}N_6O_7S_2$]$^+$ 759.2629, found 759.2630.

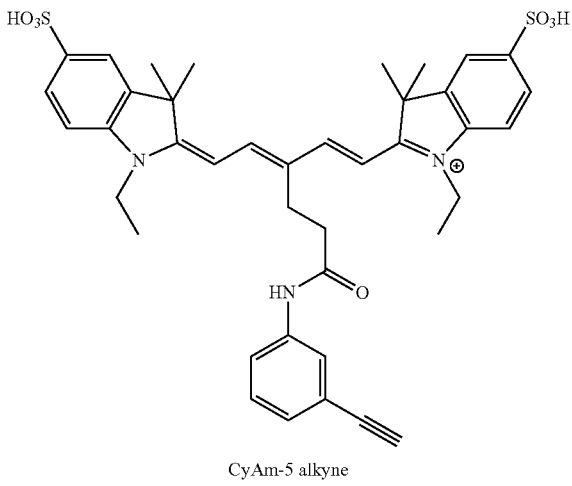 [SMILES: C#Cc1cccc(NC(=O)CCC(/C=C/C2=[N+](CC)c3ccc(S(=O)(=O)O)cc3C2(C)C)=C\C=C2\N(CC)c3ccc(S(=O)(=O)O)cc3C2(C)C)c1]

CyAm-5 alkyne (5c)

Yield 65%, 114 mg starting with 0.2 mmole of 3c. $^1$H NMR (400 MHz, DMSO-$d_6$): δ 10.14 (s, 1H), 8.25 (d, 2H, J=14.2 Hz), 7.88 (s, 2H), 7.85 (s, 1H), 7.71 (d, 2H, J=8.1 Hz), 7.54 (d, 1H, J=8.8 Hz), 7.40 (d, 2H, J=8.4 Hz), 7.31 (t, 1H, J=7.9 Hz), 6.38 (d, 2H, J=14.2 Hz), 4.26 (m, 4H), 4.12 (s, 1H), 3.05 (t, 2H, J=6.8 Hz), 2.61 (t, 2H, J=6.8 Hz), 1.74 (s, 12H), 1.23 (t, 6H, J=7.3 Hz). $^{13}$C NMR (400 MHz, DMSO-$d_6$): δ 172.81, 171.24, 153.59, 145.20, 141.57, 140.79, 139.28, 132.49, 129.14, 126.39, 126.13, 122.19, 121.91, 119.99, 119.77, 110.03, 99.83, 83.33, 80.47, 48.98, 38.70, 35.49, 26.84, 20.30, 12.11. HRMS-ESI [M]$^+$ m/z calcd. for [$C_{40}H_{44}N_3O_7S_2$]$^+$ 742.2615, found 742.2612.

Optical Properties.

Absorption spectra and extinction coefficients of the fluorophores were obtained on a Varian Cary 50-Bio UV-visible spectrophotometer. Extinction coefficients were measured in phosphate-buffered saline (PBS), 10 mM phosphate buffer pH 7.0, 27 mM potassium chloride and 137 mM sodium chloride and were averaged over at least three sets of parallel experiments. For each trail, 2-3 mg of the HPLC-purified dyes were weighed on a Mettler AT201 analytical balance with an error of ±0.01 mg and were dissolved in deionized water using a 10 mL volumetric flask to prepare the stock solutions.

Figure 3:
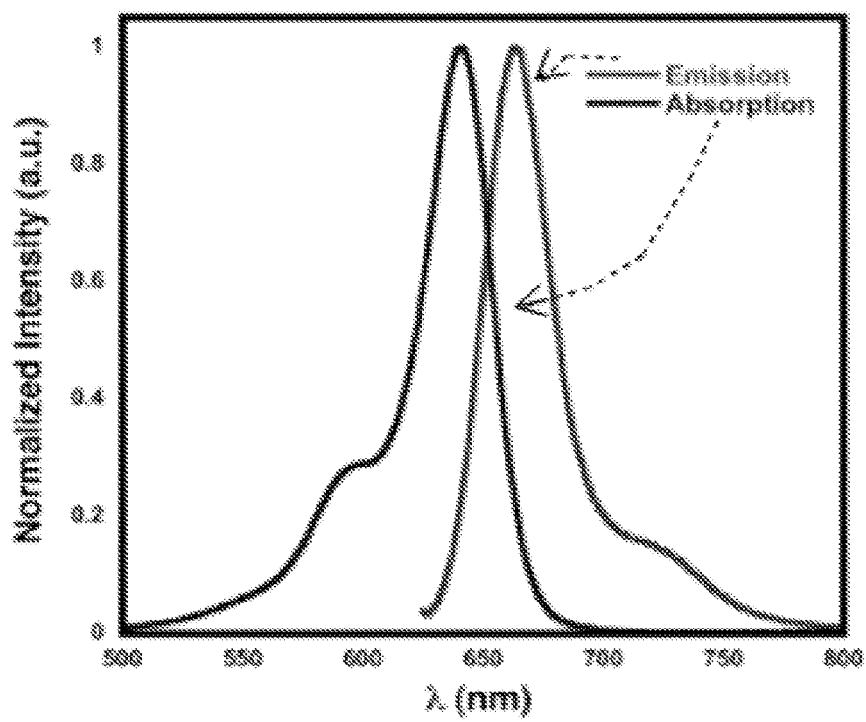
FIG. 3 shows the normalized absorption and emission spectra of CyAm-5 acid in PBS, pH 7.0.

Emission spectra were collected on a Varian Cary Eclipse fluorescence spectrophotometer. Quantum yield measurements were performed on at least eight trails for each dye derivative with maximum absorption for each sample less than 0.1, using Cy5 as a standard (Φ=0.27) (Mujumdar, R. B., Ernst, L. A., Mujumdar, S. R., Lewis, C. J., and Waggoner, A. S. (1993) Cyanine dye labeling reagents: sulfoindocyanine succinimidyl esters. *Bioconjug. Chem.* 4, 105-11). The standard deviation for both the extinction coefficient and quantum yield measurements is less than 5%. Normalized absorption and emission spectra of CyAm-5 acid in PBS, pH 7.0 is shown in FIG. 3.

Photostability data were collected on a Horiba JobinYvon Fluorolog-3 spectrofluorometer (Edison, N.Y.) equipped with a 450 W xenon lamp (Ushio inc. Japan). Dye photobleaching was observed by monitoring the fluorescence emission of absorbance matched dye samples (absorbance <0.1) at an excitation wavelength 620 nm for 60 minutes. Photostability data of CyAm-5 acid and the Cy5 standard in PBS buffer (pH 7.0) is presented in FIG. 4. After 60 minutes of irradiation at 620 nm, 42% of CyAm-5 acid (18 nM) was photobleached, whereas 54% of Cy5 at the comparable absorption was photobleached. Thus, CyAm-5 acid has 28% better photostability than Cy5.

Fluorescence Labeling and Cell Imaging.

Chinese hamster ovary (CHO) cells were maintained in a 5% $CO_2$, water-saturated atmosphere and grown in F12 HAMS medium supplemented with 10% FBS, 1% penstrep and 1% L-glutamine. For biolabeling experiments, the cells were incubated for 2-3 days in the regular medium or medium supplemented with 100 μM Ac$_4$ManNAc (Molecular probes) in an eight-well LabTek II chamber slide (Nunc). The medium was gently aspirated, and the cells were fixed at –20° C. by methanol for 10 min and then acetone for 1 min. The cells then were washed with 500 μL of PBS (pH 7.0) three times and were treated with a bioorthogonal reaction solution containing 20 μM CyAm-5 alkyne, 100 μM CuSO$_4$/100 μM Tris[(1-benzyl-1H-1,2,3-triazol-4-yl)methyl]amine (TBTA) if mentioned, and 1 mM sodium ascorbate in PBS (pH 7.0) at room temperature for 1~2 hours. Immediately prior to imaging, Vectra Shield mounting medium containing DAPI (Vector Labs) was applied to the cells. Fluorescent images were captured on a Nikon Eclipse TE2000-S fluorescence microscope with 40× objective equipped with a Photometrics Cascade 512B CCD camera using excitation and emission filters from Chroma Technology. Exposure times of 200 and 1000 ms, for the nuclear stain and carbocyanine dye channels, respectively, were used for image collection.

Figure 5:
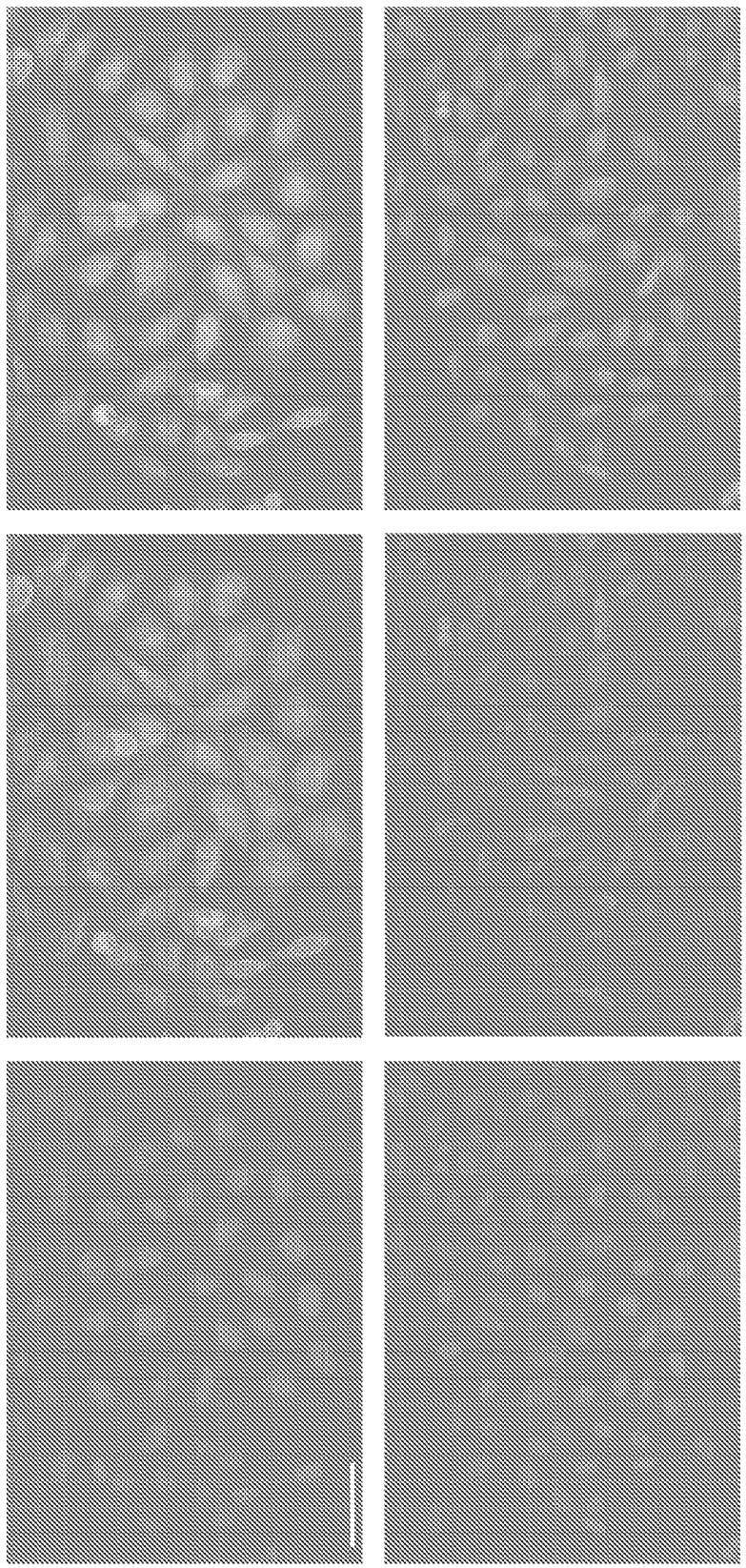
FIG. 5 shows the fluorescence microscopy of CHO cells labeled with CyAm-5 alkyne. The scale bar represents 50 μm.

FIG. 5 shows the fluorescence microscopy of CHO cells labeled with CyAm-5 alkyne. Cells incubated with azidosugar supplemented media (top) or unsupplimented media (bottom) are presented after treatment with CyAm-5 alkyne in the presence of Cu(I)/TBTA as catalyst. Cell nuclei stained with DAPI colored blue (left), fluorescence signal from CyAm-5 alkyne colored red (center) and the merged images (right) are shown. The scale bar represents 50 μm.

Figure 6A:
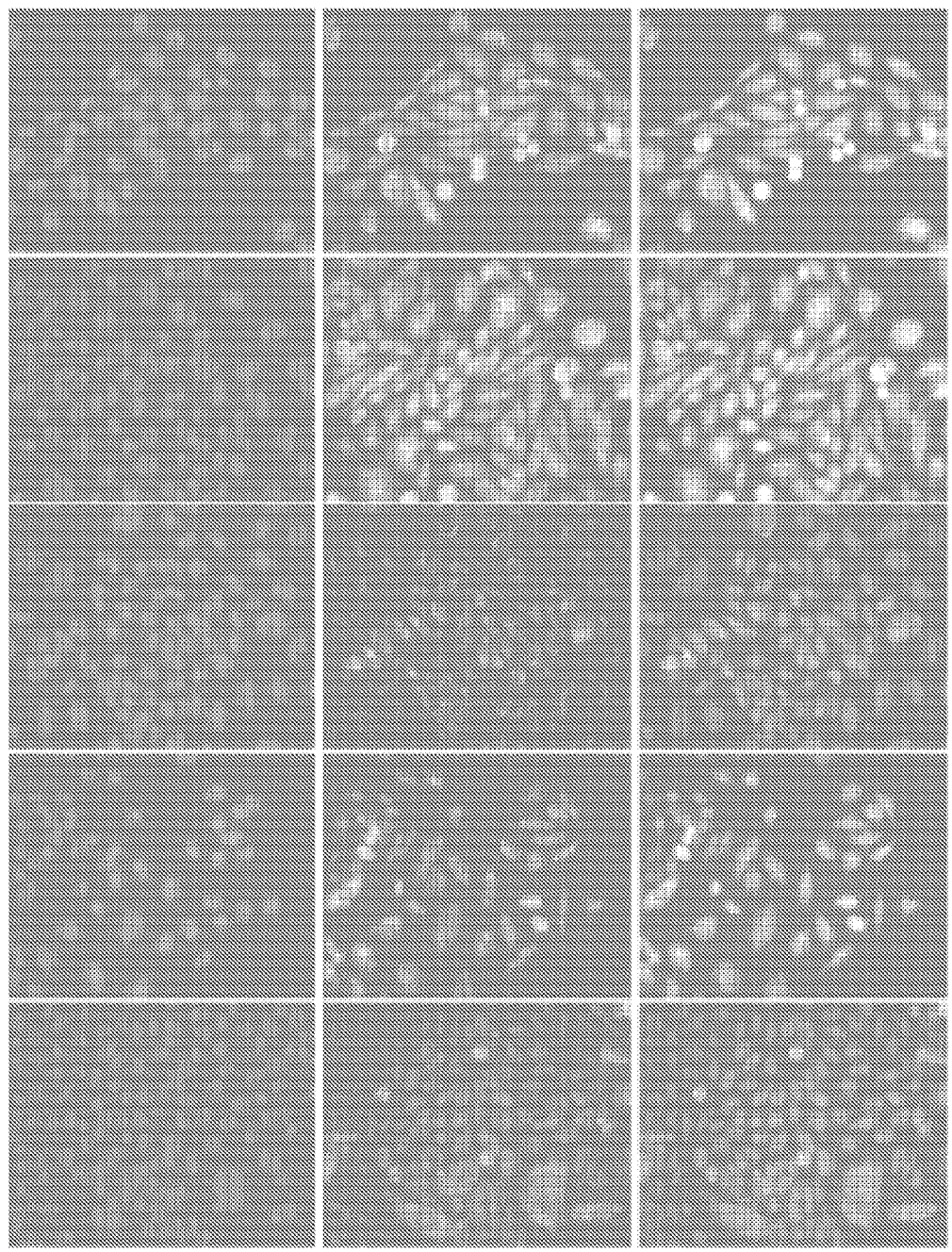
FIGS. 6A and 6B shows the fluorescence imaging of CHO cells labeled with CyAm-5 alkyne and controls.
Figure 6B:
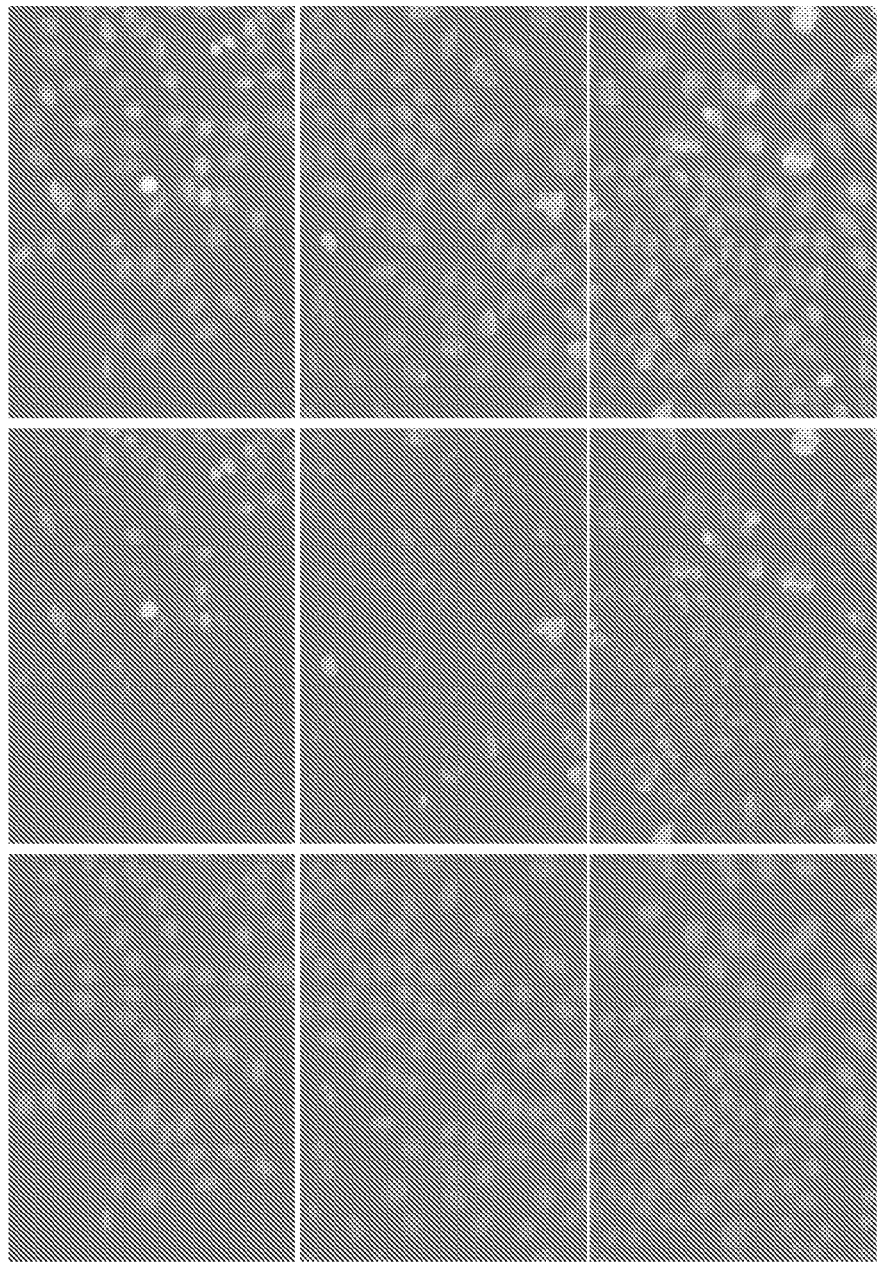

FIGS. 6A-6B show fluorescent imaging of CHO cells labeled with CyAm-5 alkyne and controls. Cells bearing azido-sugar (lanes 1-4) and regular cells (lanes 5-8) are labeled by CyAm-5 alkyne in the presence of both Cu(I) and ligand TBTA (lanes 1 and 5), Cu(I) alone (lanes 2 and 6), TBTA alone (lanes 3 and 7), or neither of the two (lanes 4 and 8). Cell nuclei stained with DAPI, fluorescence of labeled CyAm-5 alkyne and merge figures of the two above are shown in column left, middle and right, respectively.

Figures 7, 8:
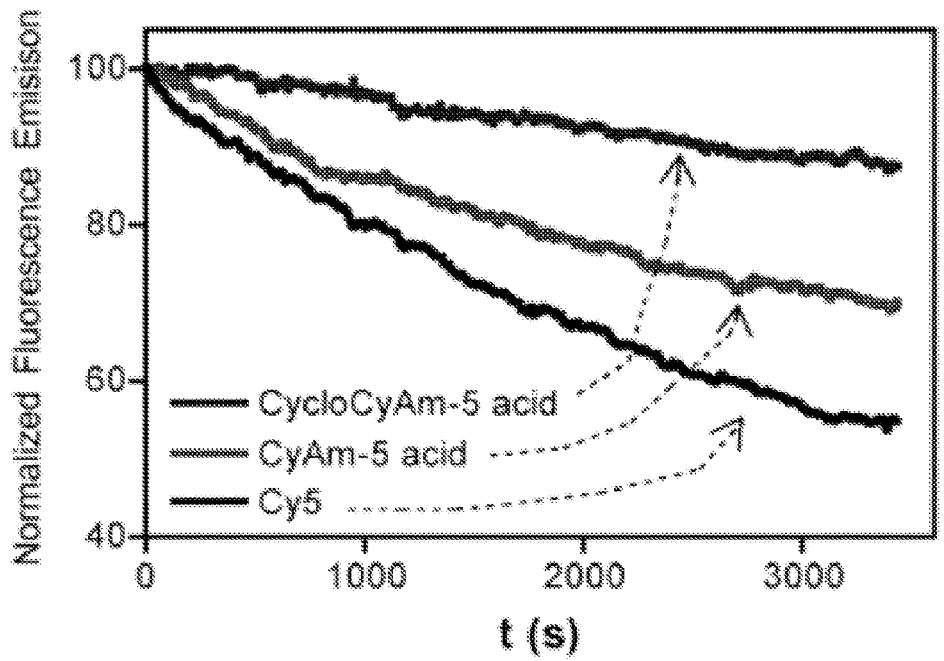
FIG. 7 shows the photostability of pentamethine carbocyanine dyes in PBS buffer (pH 7.0).
FIG. 8 summarizes the optical properties of pentamethine carbocyanine dyes, CyAm-5 acid, CyAm-5 azide, and CyAm-5 alkyne.

FIG. 7 shows the photostability of pentamethine carbocyanine dyes in PBS buffer (pH 7.0). Dye samples with the same absorption ($A_{620\ nm}$<0.1) were irradiated for an hour at 620 nm. Both bio-conjugatable new dyes, CyAm-5 acid and CycloCyAm-5 acid with photobleaching of 30% and 12%, respectively, were more photostable than Cy5 (45%).

All images from the carbocyanine dye channel were processed with identical leveling.

Combined with the simple isolation of the dyes by precipitation from diethyl ether, the overall yields for the dye condensations are all near 65% even after HPLC purification (FIG. 2). Regardless of the functional groups attached to the polymethine scaffold, the optical properties of the three dye derivatives, CyAm-5 acid (5a), CyAm-5 azide (5b), and CyAm-5 alkyne (5c) are nearly identical. Absorption and emission spectra of CyAm-5 acid are shown in FIG. 3. CyAm-5 acid has optical features of a typical pentamethine cyanine dye with absorption and emission maxima at 642 and 658 nm, respectively. The absorption and emission maxima of all three dyes are blue-shifted by approximately 5 nm in comparison to those of Cy5, whereas the stoke shifts are nearly identical to Cy5, ~16 nm. FIG. 8 summarizes the optical properties of the monofuctional dyes, CyAm-5 acid (5A), CyAm-5 azide (5B), CyAm-5 alkyne (5C). All of the three new dyes are extremely bright with extinction coefficients greater than 215,000 $M^{-1}cm^{-1}$ and quantum yields of 0.17 or higher.

Figure 4:
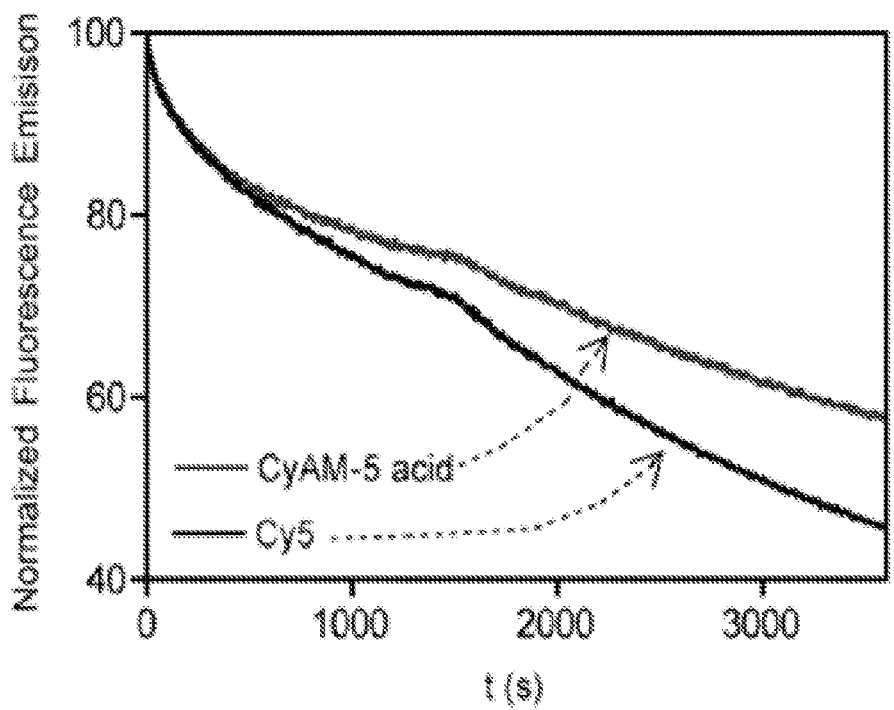
FIG. 4 shows the photostability of CyAm-5 acid and the Cy5 standard in PBS buffer (pH 7.0).

Furthermore, the new dyes have better photostability than typical cyanine derivatives that have unsubstituted polymethine chains. As shown in FIG. 4, after an hour irradiation, CyAm-5 acid shows 28% less photobleaching when compared to Cy5.

Due to their bright fluorescence, long wavelength absorption and emission as well as the ability to accommodate a variety of functional groups for conjugation reactions, this new class of cyanine dyes should find themselves useful in many biological labeling and imaging applications. For example, CyAm-5 acid can be conveniently converted to its corresponding activated succinimidyl ester (unpublished data. Reaction is complete within one hour at room temperature in the presence of 4 equiv. disuccimidyl carbonate and 4 equiv. triethylamine in anhydrous DMF) for conjugation to amine containing molecules. CyAm-5 azide and alkyne have a variety of potential uses in which they can be employed as a component in the click reaction. In addition, the aryl azide of CyAm-5 azide may find use in photocrosslinking experiments.

Recently fluorescence labeling methods based upon click chemistry have been developed for visualization of glycoproteins in cells incubated with azide containing sugars (Baskin, J. M., Prescher, J. A., Laughlin, S. T., Agard, N. J., Chang, P. V., Miller, I. A., Lo, A., Codelli, J. A., and Bertozzi, C. R. (2007) Copper-free click chemistry for dynamic in vivo imaging. *Proc. Natl. Acad. Sci. USA* 104, 16793-7; Sawa, M., Hsu, T. L., Itoh, T., Sugiyama, M., Hanson, S. R., Vogt, P. K., and Wong, C. H. (2006) Glycoproteomic probes for fluorescent imaging of fucosylated glycans in vivo. *Proc. Natl. Acad. Sci. USA* 103, 12371-6; Hsu, T. L., Hanson, S. R., Kishikawa, K., Wang, S. K., Sawa, M., and Wong, C. H. (2007) Alkynyl sugar analogs for the labeling and visualization of glycoconjugates in cells. *Proc. Natl. Acad. Sci. USA* 104, 2614-9). We have adapted this sugar labeling system to demonstrate the ability of our monofunctional dyes to conduct efficient bioorthogonal reactions in bio-relevant systems.

Azide sugar modified Chinese hamster overy (CHO) cells were first prepared by incubation of the cells with azidoacetylmannosamine containing media for 3 days. These cells then were fixed with methanol/acetone and were labeled with CyAm-5 alkyne in the presence of copper (I) as a catalyst. The cells bearing azido sialic acid in their glycoprotein showed increased fluorescence signal when compared to control cells that do not contain azido-mannosamine, as shown in FIG. 5, indicating the labeling of the cells with CyAm-5 alkyne via formation of a triazole linkage. The enhancement of fluorescence signal is only observed in the presence of both catalyst Cu(I) and azido glycans (FIG. 6A-B). The Cu(I) chelating ligand, trisbenzyltriazolylmethylamine (TBTA), facilitates the reaction, but is not necessary for efficient labeling of the cells. The requirement of both Cu(I) and azidosugar treatment for fluorescent labeling of CHO cells with CyAm-5 alkyne indicates that the resulting click reaction is a selective, bioorthongal method for cell labeling.

Example 2

Synthesis and Characterization of Exemplary Carbocyanine Dyes Based on Benzindoleninium and Indoleninium Derivatives

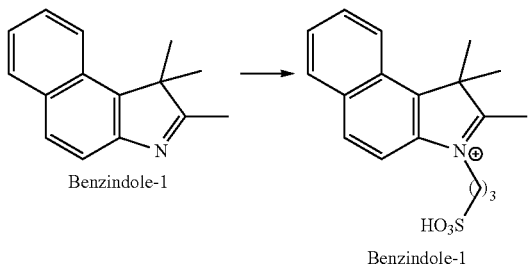 [SMILES: CC1=Nc2ccc3ccccc3c2C1(C)C ; CC1=[N+](CS(=O)(=O)O)c2ccc3ccccc3c2C1(C)C]

Benzindole-1 → Benzindole-1

Synthesis of (1,1,2-trimethyl-1H-benzo[e]indolium-3-yl)propanesulfonate: (benzindole-1)

1,1,2-trimethyl-1H-benzo[e]indole (benzindole-1, 10.43 g, 50 mmol) was dissolved in 20 mL dichlorobenzene. To the solution then was added 1,3-propanesultone (6.73 g, 55 mmol) and the mixture was heated at 155° C. in an air-tight flask for 1 hour. After cooling, the benzindoleninium was precipitated by addition of ethylacetate and was collected by filtration. The product was confirmed by LCMS and was above 99% pure. Yield: 96%, 16.6 g.

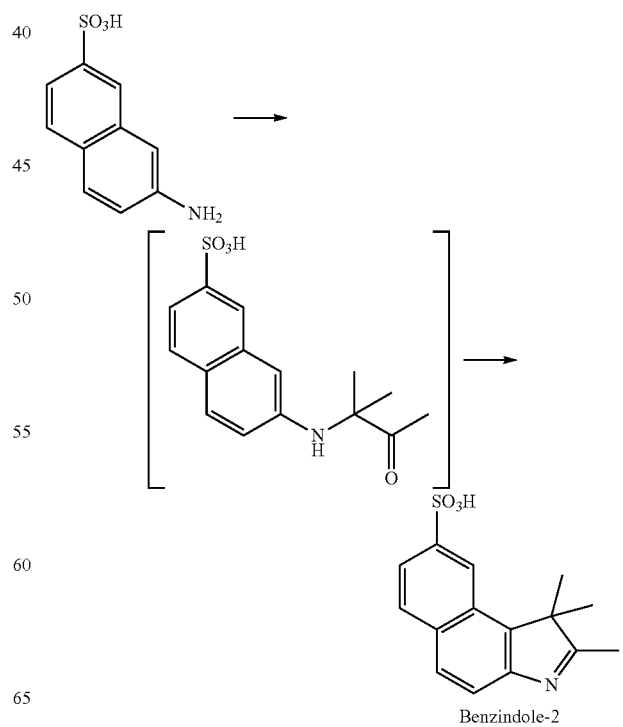

Benzindole-2

Synthesis of 1,1,2-trimethyl-1H-benzo[e]indole-8-sulfonic acid (Benzindole-2)

To 7-aminonaphthalene-2-sulfonate (19.28 g, 83 mmol) in 5 mL $H_2O$/5 mL DMF, sodium carbonate (6.35 g) was added over 30 mins to dissolve the starting naphthalene. The total volume of the reaction suspension was then brought up to 50 mL by addition of DMF. After the addition of 3-bromo-3-methylbutan-2-one (21.3 g, 0.13 mol), the reaction was heated for 48 hours at 80° C. and was monitored by LCMS. The solvent was then removed under vacuum. The resulting solids were dissolved in 50 mL $H_2O$ and the solution was acidified by addition of conc. aqueous HCl. The light pink solid was collected by filtration and resuspended in 50 mL of 10% aqueous HCl. The suspension was heated at 80° C. for 2 days until the intermediates were consumed as monitored by LCMS. Pure benzindole-2 was obtained by recrystalization from a minimum amount of hot 10% aqueous HCl. Yield: 62%, 15.4 g.

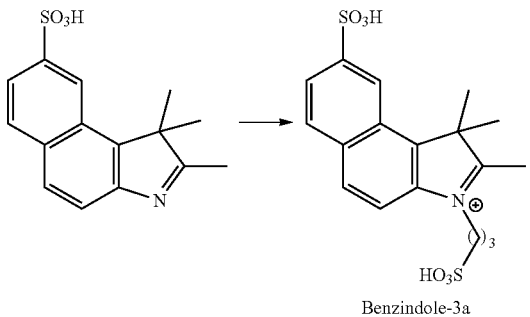 [SMILES: CC1=Nc2ccc3ccc(S(=O)(=O)O)cc3c2C1(C)C ; CC1=[N+](CS(=O)(=O)O)c2ccc3ccc(S(=O)(=O)O)cc3c2C1(C)C]

Benzindole-3a

Synthesis of 8-sulfonate-(1,1,2-trimethyl-1H-benzo[e]indolium-3-yl)propane-sulfonate (Benzindole-3a)

Benzindole-2 (2 g, 7 mmol) was dissolved in 18.5 ml of propanesultone and was heated at 190° C. in an air-tight flask for 4.5 hours. After cooling, the reaction solution was poured over 1 L acetone. The resulting solids were isolated and heated in 25 mL 10% HCl at 100° C. for 2 hours. The crude reaction was cooled and extracted over methylene chloride. The methylene chloride washes were discarded. After removal of the solvent, the crude material was dissolved in a minimum amount of methanol and was precipitated by addition of acetone. Yield: 69%, 1.97 g.

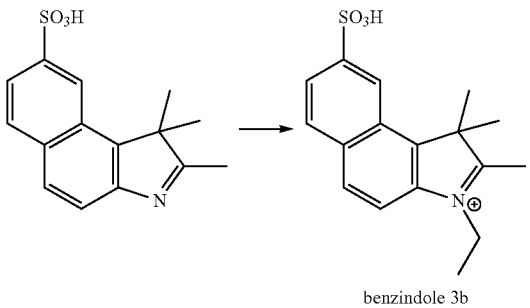 [SMILES: CC1=Nc2ccc3ccc(S(=O)(=O)O)cc3c2C1(C)C ; CC[N+]1=C(C)C(C)(C)c2c1ccc1ccc(S(=O)(=O)O)cc21]

benzindole 3b

Synthesis of 3-ethyl-1,1,2-trimethyl-8-sulfo-1H-benzo[e]indolium (Benzindole-3b)

Benzindole-2 (1 g, 3.5 mmol) was dissolved in 10 mL ethyl iodide and 20 mL anhydrous DMF. The reaction solution was submitted to microwave irradiation at 110° C. for 1 hour. The desired product was collected by filtration. Yield: 38%, 426 mg.

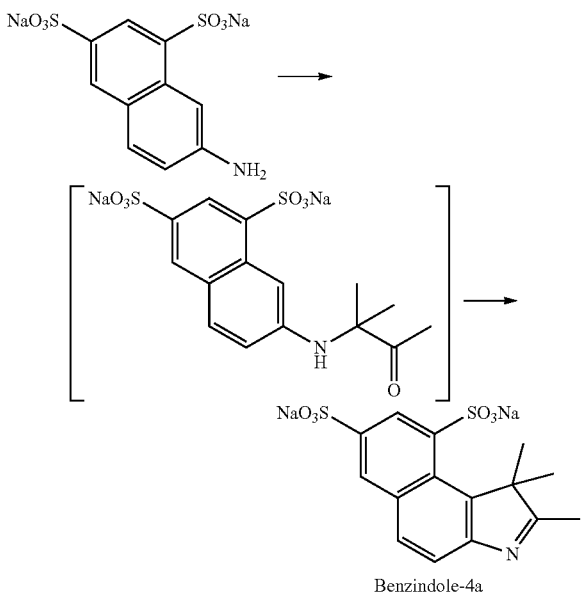

Benzindole-4a

Synthesis of Disodium 1,1,2-trimethyl-1H-benzo[e]indole-7,9-disulfonic acid (Benzindole-4a)

Disodium-6-amino-1,3-naphthalenedisulfonate (27.83 g, 80 mmol) was dissolved in 10 mL $H_2O$ and 90 mL DMF. Sodium carbonate (8.48 g, 80 mmol) was then added to the reaction solution. Following addition of 3-bromo-3-methylbutan-2-one (19.8 g, 0.12 mole), the reaction mixture was heated at 90° C. for 2 days. The solvent then was removed under vacuum. The resulting viscous gel was dissolved in 10% HCl and was incubated at 90° C. until the intermediates were completely consumed as monitored by LCMS. The crude product was obtained by removing the solvent under vacuum and was redissolved in a minimum amount of methanol. The product was then precipitated by addition of acetone and then converted to sodium salt by addition of sodium carbonate until pH 7.0. Final product was obtained in power form by pouring the methanolic solution of the benzindole into a large excess of isopropanol, followed by filtration. Yield: 52%, 15.4 g.

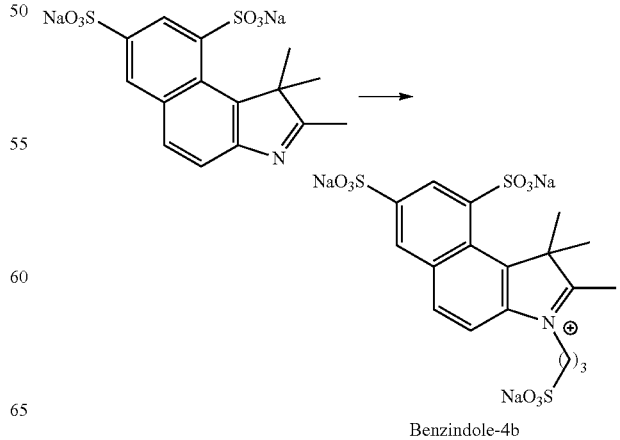

Benzindole-4b

Synthesis of 7,9-disulfonate-(1,1,2-trimethyl-1H-benzo[e]indolium-3-yl)propane-sulfonate (Benzindole-4b). Benzindole-3 (2.03 g, 5 mmole) and sodium acetate (1.22 g, 15 mmol) were dissolved in 25 mL of propanesultone and were heated at 180° C. for 3 hours. The reaction slurry was then dissolved in the minimum amount of ethanol and was precipitated by addition of acetone. The crude was collected by filtration and was stirred in 25 mL ethanol to eliminate the excess sodium acetate. Pure product was collected by filtration. Yield: (1.30 g, 47%).

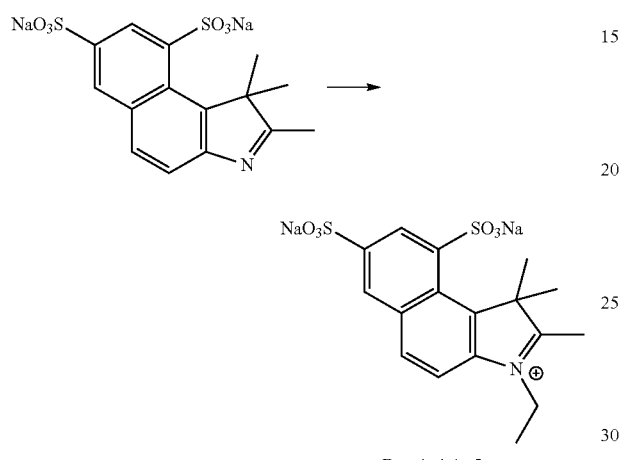

Benzindole-5

Synthesis of 3-ethyl-1,1,2-trimethyl-7,9-disulfo-1H-benzo[e]indolium (Benzindole-5)

Benzindole-3 (2.01 g, 5 mmol) was dissolved in 10 mL of ethyl iodide and 20 mL of anhydrous DMF. The reaction solution was submitted to microwave irradiation at 100° C. for 1 hour. The crude product was precipitated by addition of acetone and eluted from a C18 reverse phase cartridge with 100% $H_2O$. Yield: 29%, 632.4 mg.

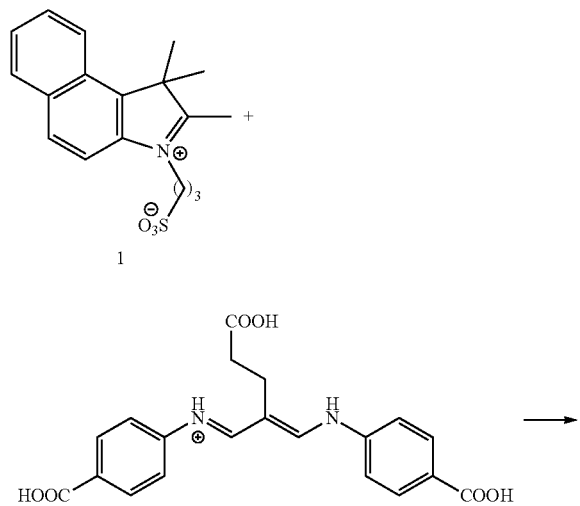

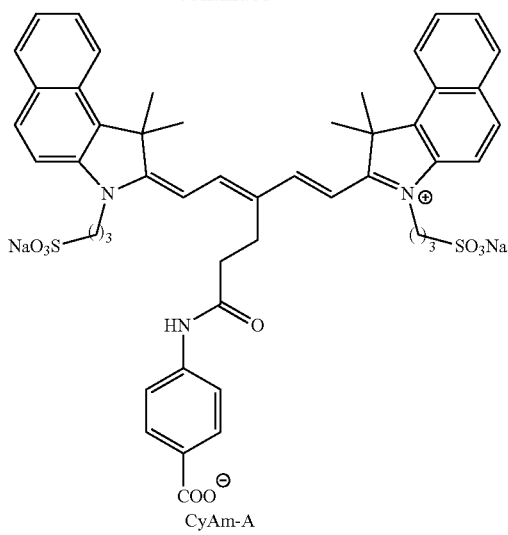

CyAm-A

Synthesis of CyAm-A

Benzindolium 1 (408 mg, 1.22 mmol) and the malonaldehyde dianil intermediate (94 mg, 0.22 mmol) were dissolved in 3 mL acetic anhydride with 5% v/v triethylamine. The reaction solution was heated in an air-tight flask at 115° C. for 1 hour. The crude dye was then precipitated by addition of diethyl ether followed by washing with diethyl ether. The crude solid was incubated in 0.1% TFA/water for 1 hour before purification on a C18 reverse phase cartridge (Isolute). Pure product was eluted from the cartridge by gradually increasing the acetonitrile concentration from 2% to 25% in 0.1% TFA/H2O. The dye was converted into its sodium salt with a cation exchange column. Yield: 42%, 98.7 mg.

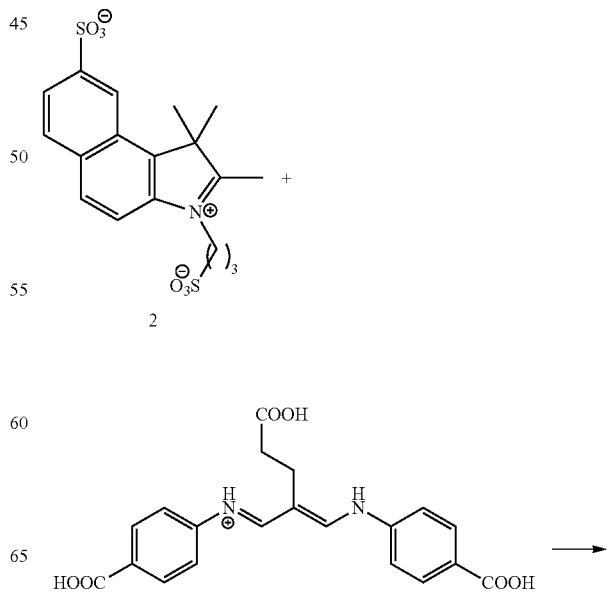

37

-continued

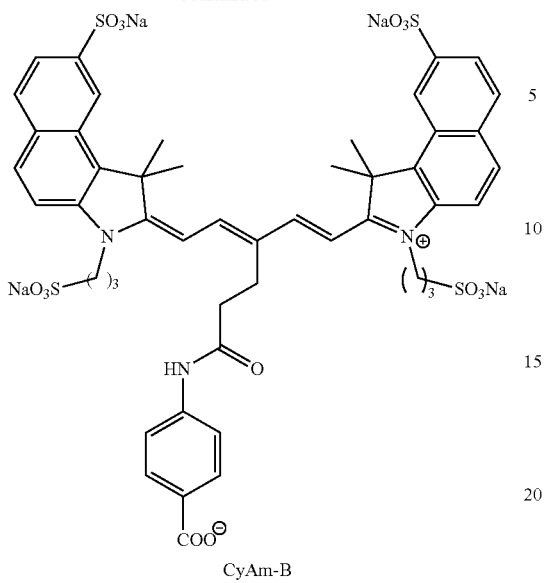

CyAm-B

Synthesis of CyAm-B

Benzindolium 2 (515 mg, 1.20 mmol) and the malonaldehyde dianil intermediate (100 mg, 0.24 mmol) were dissolved in 3 mL of acetic anhydride with 5% v/v TEA. The reaction was performed according to the procedure detailed for CyAm-A. The crude product was purified on a C18 reverse phase cartridge. The pure dye was eluted at 15% MeCN in 0.1% TFA/H2O. The dye was converted into sodium salt by cation exchange. Yield: 44%, 129.2 mg.

38

-continued

CyAm-C

Synthesis of CyAm-C

Benzindolium 3 (390.4 mg, 1.23 mmol) and the malonaldehyde dianil intermediate (95 mg, 0.22 mmol) were dissolved in 3 mL of acetic anhydride and 5% v/v TEA and were heated at 115° C. for 1 hour. The crude was worked up and purified following the procedure for CyAm-A. The pure dye was eluted with 10% MeCN in 0.1% TFA/H2O. The dye was converted into sodium salt on cation exchange. Yield: 55%, 124.2 mg.

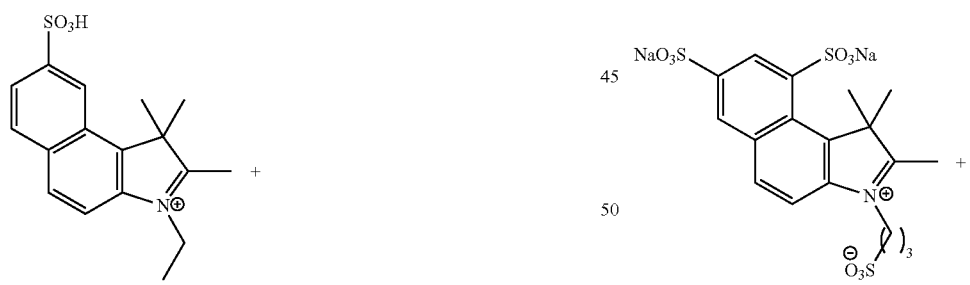

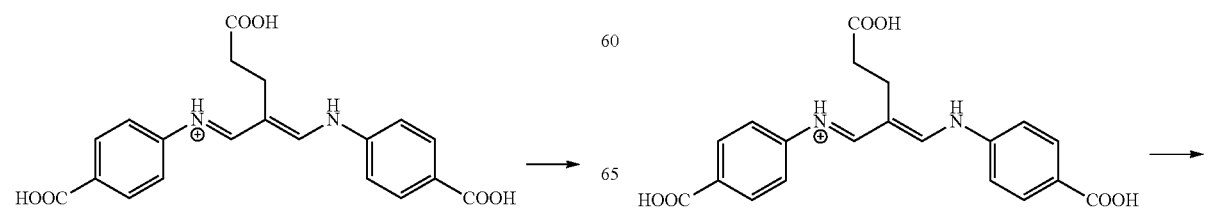

-continued

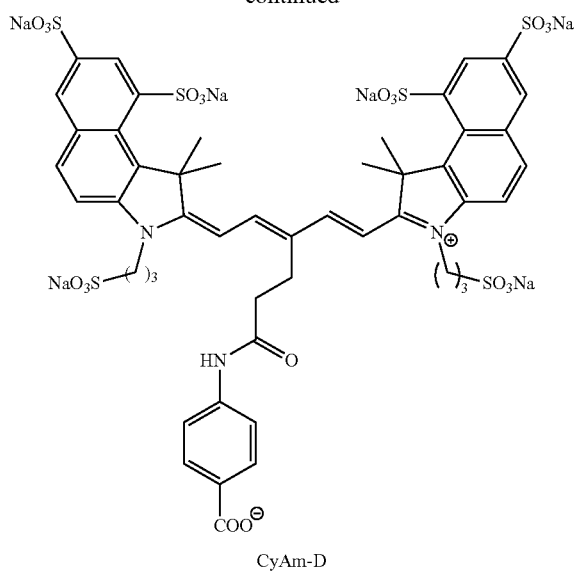

CyAm-D

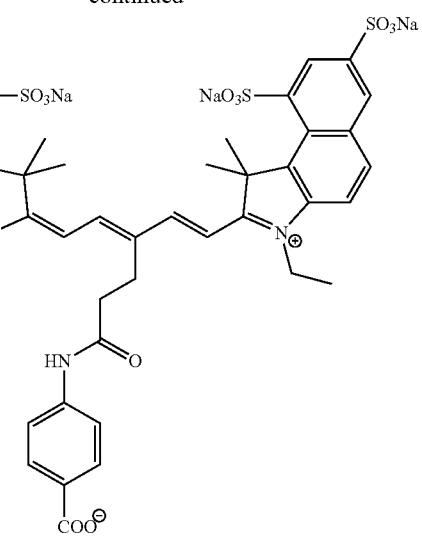

CyAm-E

Synthesis of CyAm-D

Benzindolium 4 (610.6 mg, 1.23 mmol) and the malonaldehyde dianil intermediate (95 mg, 0.22 mmol) were dissolved in 2 mL of acetic anhydride, 1 mL of acetic acid and 5% v/v TEA and were heated at 115° C. for 1 hour. The crude product was worked up following the procedure used for CyAm-A. A C18 reverse phase cartridge (Varian) was used to purify the crude material. The pure dye was eluted with 5% MeCN in 0.1% TFA/H2O. The dye was converted into its sodium salt by cation exchange. Yield: 43%, 146.9 mg.

Synthesis of CyAm-E

Benzindolium 3 (393.6 mg, 0.9 mmol) and the malonaldehyde dianil intermediate (49 mg, 0.11 mmol) were dissolved in 3 mL of acetic anhydride and 5% v/v TEA and were heated at 115° C. for 1 hour. The crude was worked up and purified following the procedure used for CyAm-A. The pure dye was eluted with 10% MeCN over 0.1% TFA/H2O. The dye was converted into its sodium salt by cation exchange. Yield: 54%, 77.1 mg.

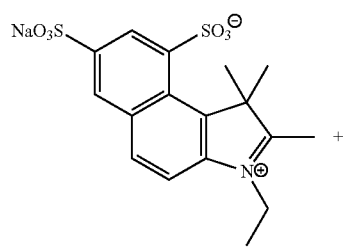

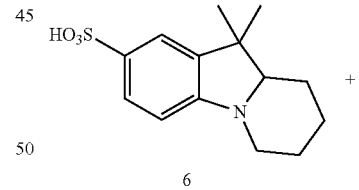

6

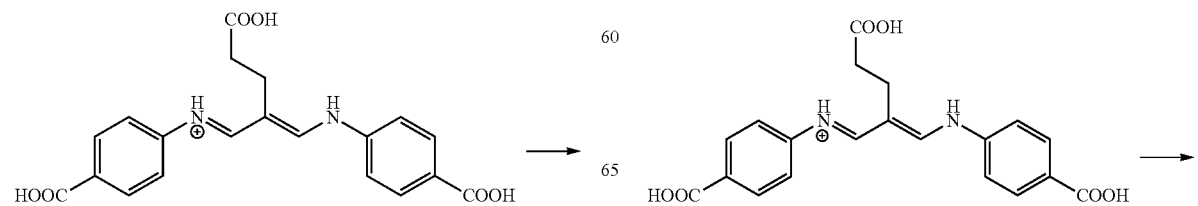

41

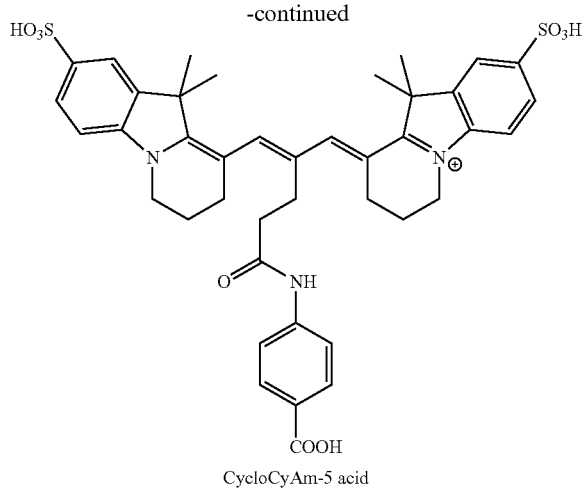

CycloCyAm-5 acid

Synthesis of CycloCyAm-5 Acid

The dye was synthesized by following the procedure reported for the CyAm-5 dyes. Indoleninium 6 (0.2 mmol) and malonaldehyde dianil acid derivative (0.05 mmol) were dissolved in 2 mL of a 2:1 acetic anhydride/acetic acid mixture containing 1% TEA. The reaction solution was heated at 115° C. for 1 hour. After cooling, the crude products were precipitated by copious diethyl ether and were purified by preparative HPLC.

FIG. 7 illustrates the photostability of exemplary pentamethine carbocyanine dyes in PBS buffer (pH 7.0). Dye samples with the same absorption ($A_{620\ nm}$<0.1) were irradiated for an hour at 620 nm. Both bio-conjugatable new dyes, CyAm-5 acid and CycloCyAm-5 acid, which show photobleaching of 30% and 12%, respectively, are more photostable than Cy5 (45%).

Example 3

Synthesis of CyAl-5 and CyAl-5.5

Synthesis of Synthesis of 7-(phenylamino)-6-((E)-(phenylimino)methyl)hept-6-enoic acid hydrochloride (1)

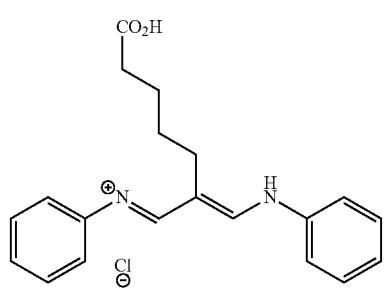

Phosgene (50 mmol of a 20% w/w solution in toluene) was added to N,N-dimethylformamide (3.9 mL, 50 mmol) with stirring in an ice bath over 5 min to give a white paste. This mixture was allowed to stand until no further gas evolution was observed (~30 min). Methyl 7,7-dimethoxyheptanoate (5.1 g, 25 mmol), prepared from cycloheptene following a published method (Claus, R. E., and Schreiber, S. L. (1986) Ozonolytic cleavage of cycloheptene to terminally differentiated products: methyl 6-oxohexanoate, 6,6-dimethoxyhexanal, methyl 6,6-dimethoxyhexanoate. Organic Syntheses 64, 150-156.), was then added dropwise to the reaction solution followed by heating at 70° C. for 1 hour. After cooling, the solvent was removed by rotary evaporation giving a yellow-brown oil. The oil was suspended in water (20 mL) then 5 mL of 10% aqueous HCl and aniline hydrochloride (6.5 g, 50 mmol) were added. The resulting mixture was sealed in a thick-walled glass pressure tube and heated at 120° C. in an oil bath for 1.5 hours. After heating, the reaction solution was cooled slowly to room temperature over 2 hours, during which the product crystallized (if the reaction is cooled too quickly, a sticky precipitate is formed instead). After filtration and washing with water, 1 is obtained as a yellow solid (2.05 g, 23%). $^1$H NMR (400 MHz, DMSO-$d_6$): δ 8.72 (d, 2H, J=12 Hz), 7.58 (d, 4H, J=8.4 Hz), 7.51 (t, 4H, J=8.0 Hz), 7.30 (t, 4H, J=7.2 Hz), 2.77 (t, 2H, J=6.4 Hz), 2.27 (t, 2H, J=7.6 Hz), 1.71-1.64 (m, 2H), 1.50-1.42 (m, 2H). HRMS-ESI [M]$^+$ m/z calcd. for [$C_{20}H_{23}N_2O_2$]$^+$ 323.1754, found 323.1743.

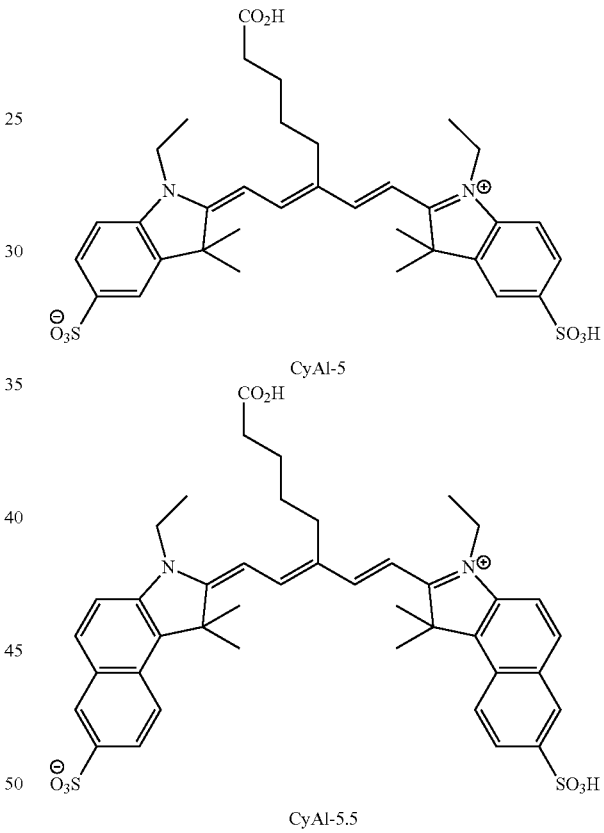

CyAl-5

CyAl-5.5

Synthetic Protocol for CyAl-5 (an Analogous Protocol is Used to Prepare CyAl-5.5)

Four equivalents of indoleninium 2 (107 mg, 0.4 mmol) or benzindolenium was dissolved with one equivalent of 1 (32 mg, 0.1 mmol) in 1 mL acetic acid/acetic anhydride/triethylamine (5:5:1). The dye was then formed by heating the reaction solution at 110° C. for 45 minutes in a sealed thick-walled glass pressure tube. The crude fluorophore was purified by C18 cartridge chromatography eluting with 30% acetontrile and 0.1% trifluoroacetic acid in water. CyAl-5. Yield, 39%. $^1$H NMR (400 MHz, DMSO-$d_6$): δ 8.18 (d, 2H, J=14 Hz), 7.82 (s, 2H), 7.65 (d, 2H, J=8.2 Hz), 7.35 (d, 2H, J=8.4 Hz), 6.18 (d, 2H, J=14 Hz), 4.24-4.19 (m, 4H), 2.63 (t, 2H, J=7.4 Hz), 2.31 (t, 2H, J=8.0 Hz), 1.71 (s, 12H), 1.68 (t, 2H, J=7.8 Hz), 1.50-1.47 (m, 2H), 1.28 (t, 6H, J=7.2 Hz). HRMS-ESI [M-2H]$^-$ m/z calcd. for [$C_{34}H_{41}N_2O_9S_2$]$^-$ 669.2310, found 669.2252. CyAl-5.5. Yield, 40%. $^1$H NMR (400 MHz, DMSO-$d_6$): δ 8.27-8.24 (m, 4H), 8.20 (d, 2H, J=8.8 Hz), 8.16 (d, 2H, J=8.8 Hz), 7.87 (d, 2H, J=8.6 Hz), 7.76 (d, 2H, J=8.8 Hz), 6.21 (d, J=14.3 Hz), 4.31 (m, 4H), 2.68-2.64 (m, 2H), 2.09 (t, 2H, J=7.0 Hz), 1.99 (s, 12H), 1.71 (t, 2H, J=6.6 Hz), 1.53 (t, 2H, J=7.2 Hz), 1.36 (t, 6H, J=7.0 Hz). HRMS-ESI [M-2H]$^-$ m/z calcd. for [$C_{42}H_{45}N_2O_9S_2$]$^-$ 769.2623, found 769.2493.

FIG. 9 summarizes the optical properties of CyAl-5 and CyAl-5.5. Spectra were obtained in phosphate buffered solution, pH 7.0. The extinction coefficients, at the dye absorption maxima, were performed in triplicate. Emission spectra were excited at 620 nm for CyAl-5 and 640 nm for CyAl-5.5. CyAl-5 and CyAl-5.5, Cy5 and Cy5.5 were used as fluorescence standards, respectively. The data are the average of at least 8 replicates and errors were <5%.

Purification of CyAl-5 (A) and CyAl-5.5 (B)

Figure 10A:
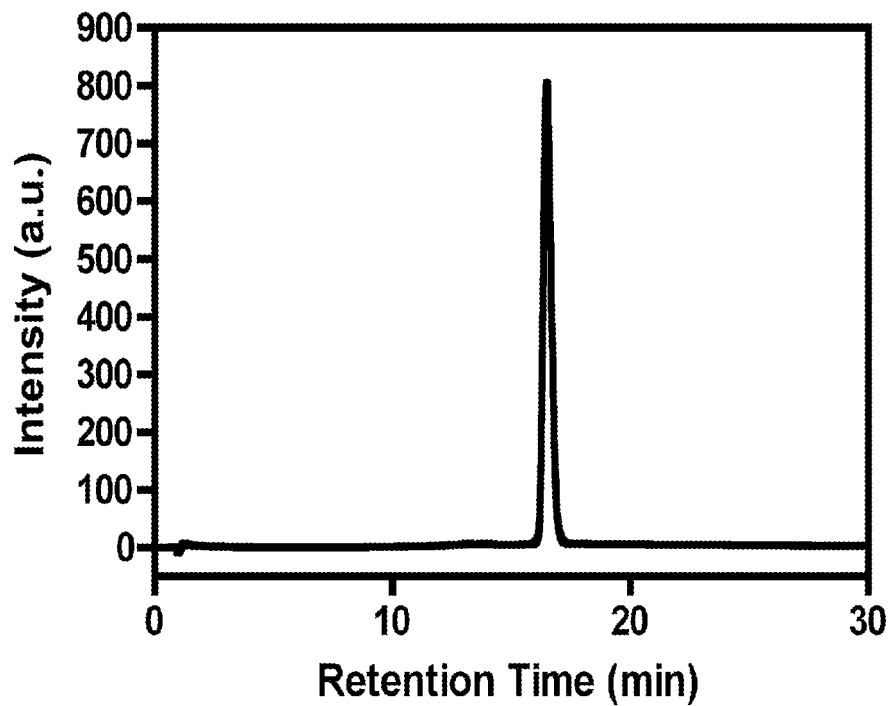
FIGS. 10A and 10B show the HPLC traces for CyAl-5 and CyAl-5.5, respectively.
Figure 10B:
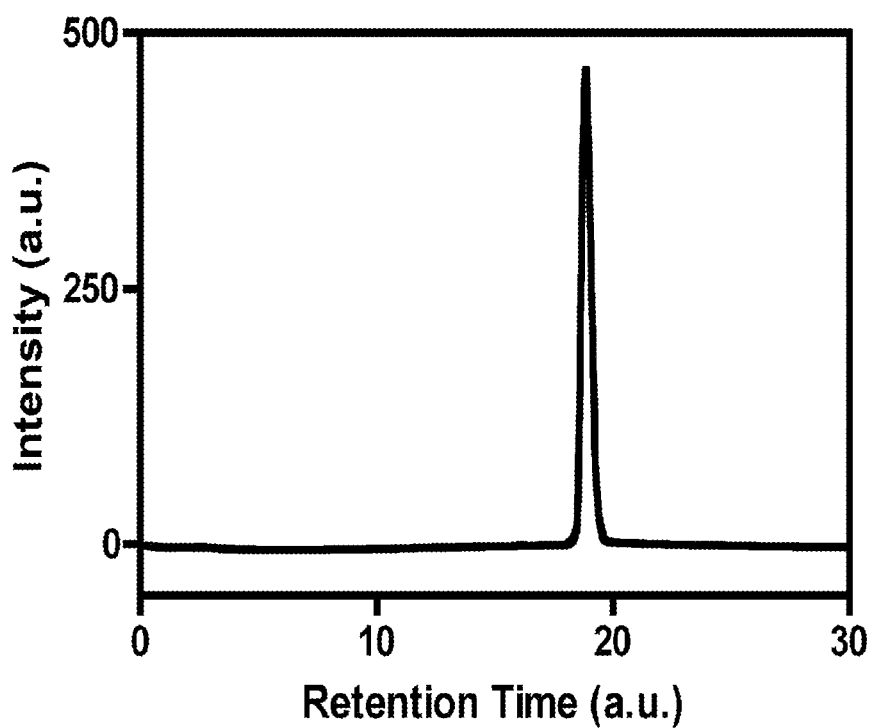

Both CyAl-5 and CyAl-5.5 were easily purified with high purity by reverse phase column chromatography using inexpensive pre-packed C18 cartridges (FIGS. 10A and 10B, respectively). CyAl-5 and CyAl-5.5 were eluted by acetonitrile/water/0.1% trifluoroacetic acid solution (0-100% acetonitrile over 30 minutes) and were suitable for both chemical and optical characterization. Both fluorophores were easily converted into their corresponding reactive succinimidyl esters by treatment with 4 equivalents disuccinimidylcarbonate and 8 equivalents of triethylamine in anhydrous DMF.

Preparation of the Activated Esters of CyAl-5 (A) and CyAl-5.5 (B).

Both CyAl-5 and CyAl-5.5 can be converted into their corresponding N-hydroxysuccinimidyl esters by treatment with 4 equivalents disuccinimidylcarbonate and 8 equivalents of triethylamine in anhydrous DMF overnight. The activated dye products are isolated by precipitation from the reaction mixture with diethyl ether.

Absorption and Emission of CyAl-5 (A) and CyAl-5.5 (B)

Figure 11A:
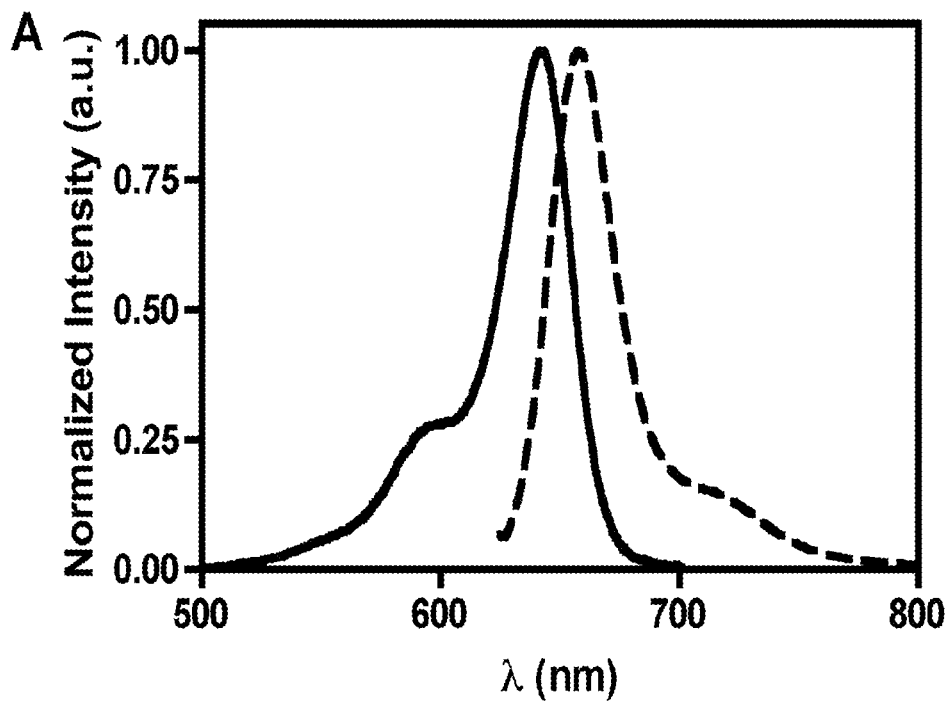
FIGS. 11A and 11B show the absorption (solid lines) and emission (dashed lines) spectra of CyAl-5 and CyAl-5.5 in PBS, pH 7.0, respectively.
Figure 11B:
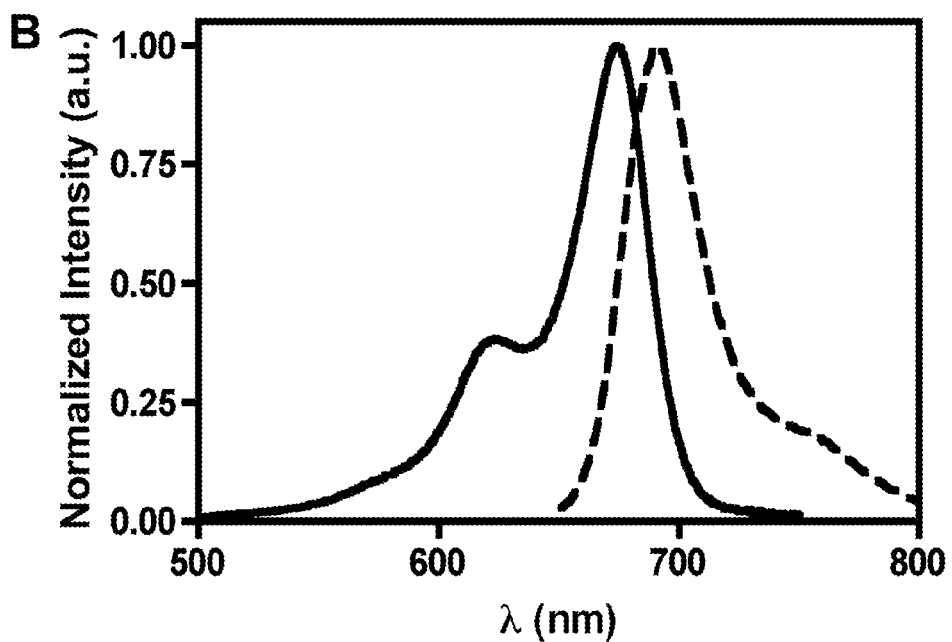

The modified fluorophores maintained optical properties that were consistent with carbocyanine dyes. FIGS. 11A and 11B show the absorption (solid lines) and emission (dashed lines) spectra of CyAl-5 (A) and CyAl-5.5 (B) in PBS, pH 7.0, respectively. CyAl-5 and CyAl-5.5 had absorption and emission spectra in far-red to near infrared region that matched well with common filter sets used for imaging commercially available Cy 5 and Cy 5.5 (As indicated on www.gelifesciences.com, λabs/λem for Cy5 and Cy5.5 are 646/664 nm and 673/693 nm, respectively). The new dyes were bright with extinction coefficients of 233,000 and 157,000 M$^{-1}$ cm$^{-1}$ and quantum yields of 13 and 12% for CyAl-5 and CyAl-5.5, respectively.

Photostability of CyAl-5 (A) and CyAl-5.5 (B)

Figure 12A:
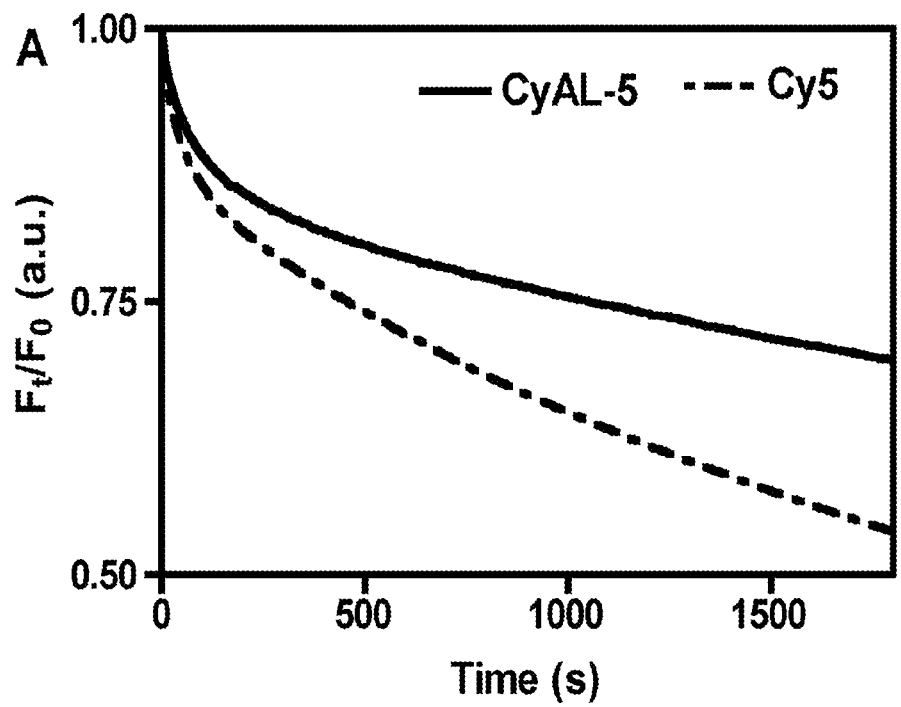
FIGS. 12A and 12B show the photostability of CyAl-5 and CyAl-5.5 in PBS buffer (pH 7.0).
Figure 12B:
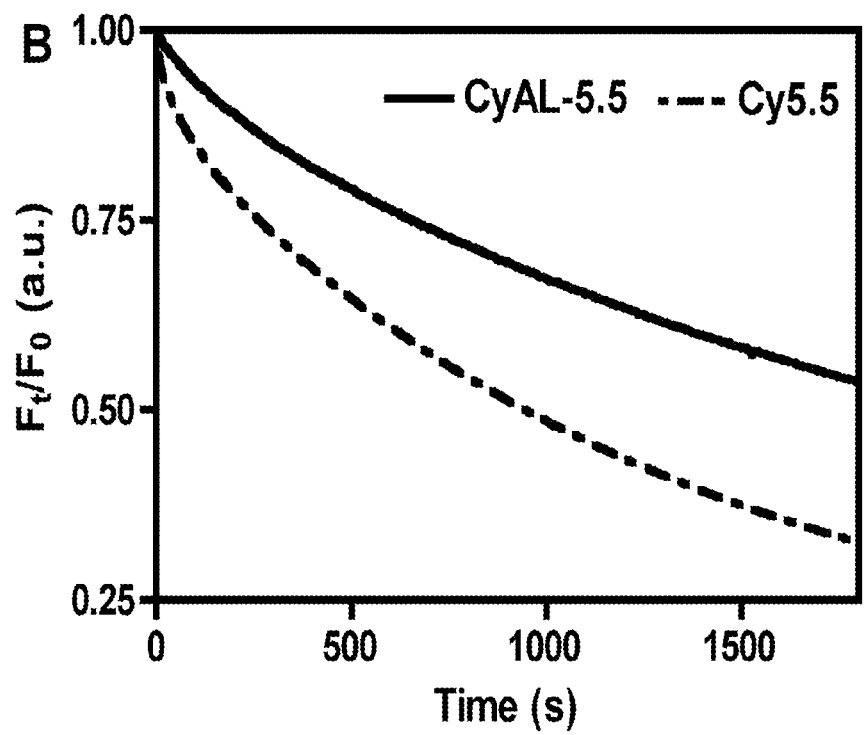

Relatively poor photostability is one disadvantage to the use of carbocyanine dyes for bioimaging. This is particularly important to imaging applications requiring continuous irradiation or use of high power laser excitation. Both CyAl-5 and CyAl-5.5 show improved photostability with 21% and 56% less photodecomposition after irradiation for 30 minutes, with respect to Cy5 and Cy5.5 standards, respectively (FIGS. 12A and 12B, respectively). Alkylation on the polymethine chain significantly improved the photostability of the cyanine dyes, especially of those with large aromatic end groups.

Example 4

Synthesis of CyAm-7

Synthesis of 4-((1E,3E)-6-carboxy-4-((E)-(4-carboxyphenylimino)methyl)hexa-1,3-dienylamino)benzoic acid hydrobromide

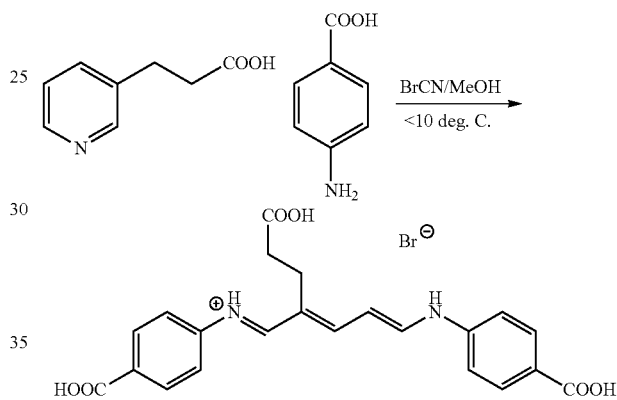

3-Pyridinepropionic acid (10 mmol, 1.52 g) and 4-aminobenzoic acid (20 mmol, 2.74 g) were dissolved in 75 mL methanol on an ice water bath. Cyanogen bromide (10 mmol, 1.07 g) in 5 mL methanol was then added to the reaction solution over 5 min. The product, (1.02 g, 21%), was collected by filtration after stirring for 2 hours and was washed with dichloromethane. $^1$H NMR (500 MHz, DMSO-$d_6$): δ 12.40 (s, 3H), 7.95-7.83 (m, 5H), 7.67-7.65 (m, 1H), 7.17 (d, 2H, J=8.0 Hz), 7.09 (d, 2H, J=8.5 Hz), 6.95 (d, 1H, J=10.5 Hz), 6.17 (t, 1H, J=12.3 Hz), 2.71 (t, 2H, J=7.5 Hz), 2.40 (t, 2H, J=7.8 Hz). ESI [M+H]$^+$ m/z calcd. for [$C_{22}H_{27}N_2O_6$]$^+$ 409.4, found 409.3.

Synthesis of CyAm-7

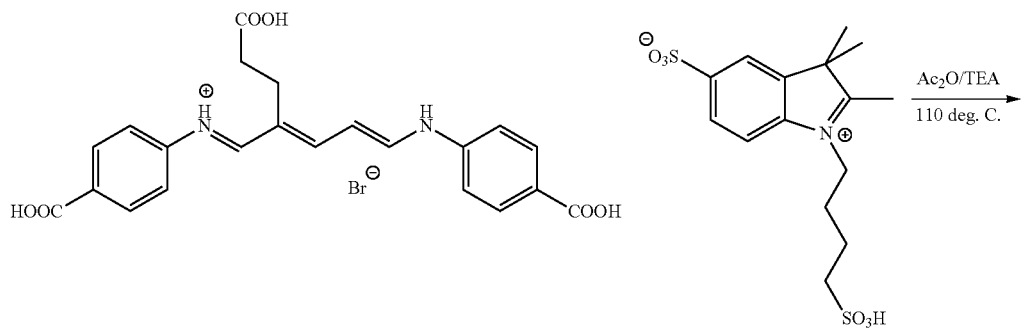

-continued

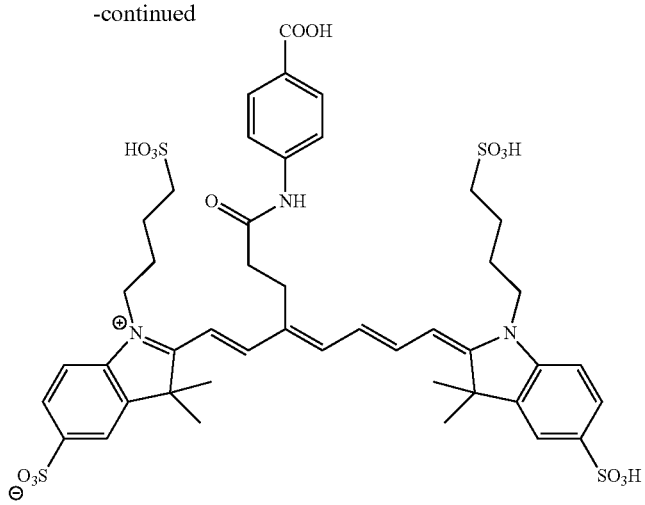

To a solution of 4-((1E,3E)-6-carboxy-4-((E)-(4-carboxyphenylimino)methyl)-hexa-1,3-dienylamino)benzoic acid hydrobromide (165.6 mg, 0.33 mmol) in acetic acid (2 mL) and triethylamine (0.2 mL) was added 2,3,3-trimethyl-1-(4-sulfobutyl)-3H-indolium-5-sulfonate (423.7 mg, 1.02 mmol). The reaction mixture was stirred at 110° C. for 30 min. After cooling, the reaction was precipitated by addition of diethyl ether and was purified by reverse phase chromatography (C18 silica). Pure CyAm-7 (186 mg, 55%) was eluted with water containing 15% acetonitrile and 0.1% TFA. $^1$H NMR (400 MHz, DMSO-$d_6$): δ 7.99 (t, 1H, J=), 7.85 (d, 2H, J=6 Hz), 7.77 (s, 4H), 7.70 (d, 2H, J=8.7 Hz), 7.65 (d, 2H, J=8.4 Hz), 7.37-7.32 (m, 2H), 4.14 (m, 4H), 2.9 (m, 2H), 2.60-2.52 (m, 6H), 1.90-1.76 (m, 8H), 1.65 (s, 12H). HRMS-ESI [M+Na]$^{2-}$ m/z (z=2) calcd. for [C$_{45}$H$_{50}$N$_3$O$_{15}$S$_4$Na]$^{2-}$ 511.6017, found 511.6017.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A carbocyanine dye, or a pharmaceutically acceptable salt thereof, selected from the group consisting of:

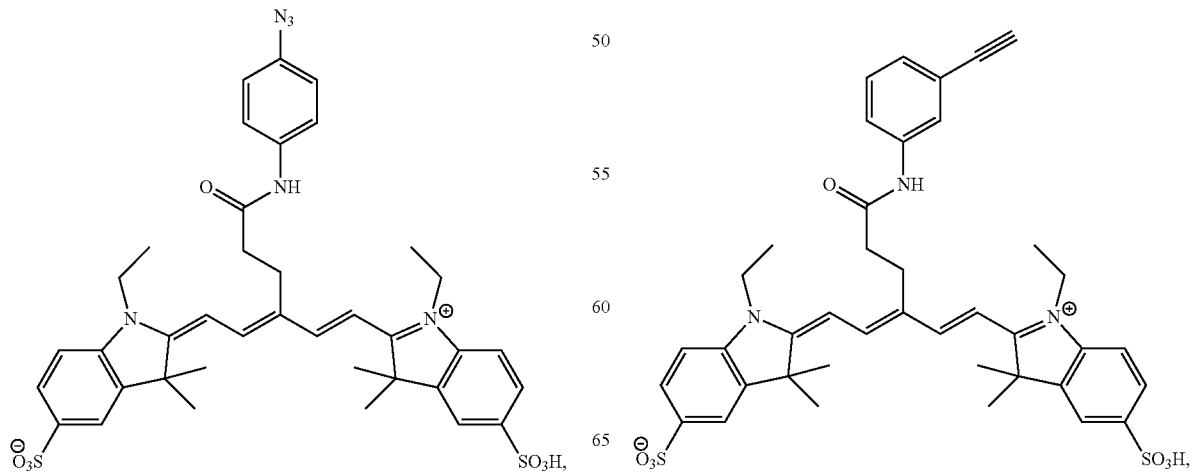

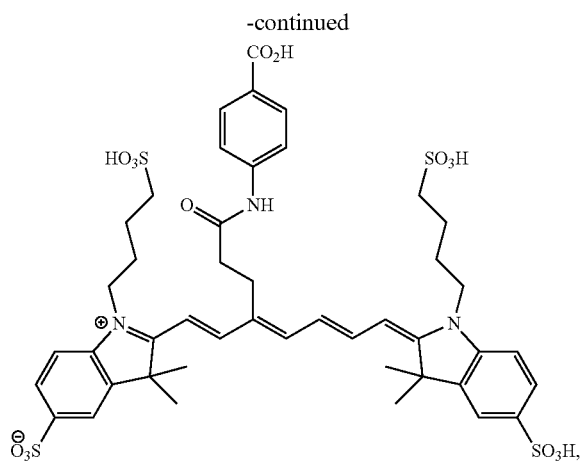

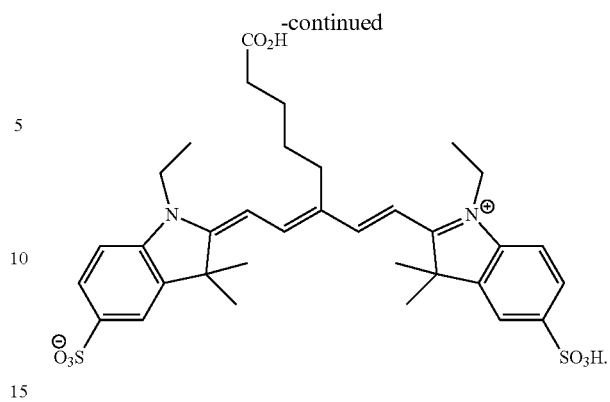

2. An in vitro or in vivo method of imaging a biological target, the method comprising:
contacting a targeting agent with a carbocyanine dye of claim 1, or a pharmaceutically acceptable salt thereof, to produce a labeled targeting agent;
administering the labeled targeting agent to a sample or a subject; and
generating a fluorescence image of the sample or the subject.

3. The method of claim 2, wherein the targeting agent is selected from the group consisting of antibodies, proteins, peptides, nucleic acids, aptamers, and surface-modified nanoparticles.

4. The method of claim 2, wherein the fluorescence image is generated by fluorescence microscopy.

5. The method of claim 2, wherein the method is carried out in vivo in a living cell.

6. The method of claim 2, wherein the biological target and the carbocyanine dye react via a 1,3-dipolar cycloaddition reaction.

* * * * *

UNITED STATES PATENT AND TRADEMARK OFFICE
CERTIFICATE OF CORRECTION

| | | |
|---|---|---|
| PATENT NO. | : 8,916,137 B2 | Page 1 of 1 |
| APPLICATION NO. | : 13/127894 | |
| DATED | : December 23, 2014 | |
| INVENTOR(S) | : Scott A. Hilderbrand, Ralph Weissleder and Fangwei Shao | |

It is certified that error appears in the above-identified patent and that said Letters Patent is hereby corrected as shown below:

In the Specification

In column 1, line 8, delete "1-01-HL080731" and insert -- 1-U01-HL080731 --, therefor.

In column 1, line 18-19, after "2008," delete "the entire contents of which are hereby incorporated by reference".

Signed and Sealed this
Ninth Day of June, 2015

Michelle K. Lee
*Director of the United States Patent and Trademark Office*